United States Patent
Wada et al.

(10) Patent No.: US 11,348,684 B2
(45) Date of Patent: May 31, 2022

(54) SURGICAL SUPPORT SYSTEM, INFORMATION PROCESSING METHOD, AND INFORMATION PROCESSING APPARATUS

(71) Applicant: Sony Corporation, Tokyo (JP)

(72) Inventors: Seiji Wada, Kanagawa (JP); Kunihiko Akiyoshi, Saitama (JP)

(73) Assignee: Sony Corporation, Tokyo (JP)

( * ) Notice: Subject to any disclaimer, the term of this patent is extended or adjusted under 35 U.S.C. 154(b) by 82 days.

(21) Appl. No.: 16/631,851

(22) PCT Filed: Jul. 5, 2018

(86) PCT No.: PCT/JP2018/025458
§ 371 (c)(1),
(2) Date: Jan. 17, 2020

(87) PCT Pub. No.: WO2019/021781
PCT Pub. Date: Jan. 31, 2019

(65) Prior Publication Data
US 2020/0168325 A1  May 28, 2020

(30) Foreign Application Priority Data
Jul. 24, 2017 (JP) .............................. JP2017-142420

(51) Int. Cl.
*G16H 40/63* (2018.01)
*A61B 34/00* (2016.01)
*G16H 40/20* (2018.01)

(52) U.S. Cl.
CPC ............ *G16H 40/63* (2018.01); *A61B 34/25* (2016.02); *G16H 40/20* (2018.01); *A61B 2034/252* (2016.02); *A61B 2034/254* (2016.02)

(58) Field of Classification Search
CPC ........ G16H 40/63; G16H 40/20; G16H 40/60; A61B 34/25; A61B 2034/252; A61B 2034/254
See application file for complete search history.

(56) References Cited

U.S. PATENT DOCUMENTS

2012/0075464 A1* 3/2012 Derenne ................. A61B 5/112
348/135
2014/0081659 A1* 3/2014 Nawana ................ A61B 5/1118
705/3

(Continued)

FOREIGN PATENT DOCUMENTS

| EP | 2945087 A2 | 11/2015 |
| WO | 2015/066565 A1 | 5/2015 |
| WO | 2017/083768 A1 | 5/2017 |

OTHER PUBLICATIONS

International Search Report and Written Opinion dated Oct. 11, 2018 for PCT/JP2018/025458 filed on Jul. 5, 2018, 11 pages.

(Continued)

*Primary Examiner* — Mallika D Fairchild
*Assistant Examiner* — Shreya Anjaria
(74) *Attorney, Agent, or Firm* — Xsensus LLP

(57) ABSTRACT

Provided is a surgical support system including: a camera installed in an operating room; and an information processing apparatus including processing circuitry configured to compare reference data that is related to at least one reference person or reference device in the operating room and that is generated from observation of the operating room, with first feature data related to a first person or a first device extracted from a first image captured by the camera installed in the operating room.

18 Claims, 15 Drawing Sheets

(56) References Cited

U.S. PATENT DOCUMENTS

| 2016/0253802 A1* | 9/2016 | Venetianer | G06K 9/00771 |
| | | | 382/128 |
| 2016/0270861 A1* | 9/2016 | Guru | A61B 34/20 |
| 2019/0090969 A1* | 3/2019 | Jarc | A61B 90/361 |

OTHER PUBLICATIONS

Bardram, J., E., et al., "Phase recognition during surgical procedures using embedded and body-worn sensors," IEEE International Conference on Pervasive Computing and Communications (PerCom), IEEE, Seattle, WA, USA, Mar. 21-25, 2011, pp. 45-53.

Charriere, K., et al., "Automated Surgical Step Recognition in Normalized Cataract Surgery Videos," 36th Annual International Conference of the IEEE Engineering in Medicine and Biology Society, IEEE, Chicago, IL, USA, Aug. 26-30, 2014, pp. 4647-4650.

* cited by examiner

Fig. 13

| SURGERY STAGE | SMALL CLASSIFICATION | MAIN DOCTOR | OTHER ASSOCIATED PERSONNEL | EVENT |
|---|---|---|---|---|
| ANESTHESIA INTRODUCTION | | ANESTHESIOLOGIST | ANESTHESIOLOGICAL ASSISTANT, NURSE | ANESTHESIA INTRODUCTION |
| | | ANESTHESIOLOGIST | ABOUT 5 PERSONS | CHANGE OF POSITION OF PATIENT, BED MOVEMENT |
| NAVIGATION | HEAD FIXING | SURGEON | 2 TO 3 ASSISTANTS | HEAD FIXING |
| | REGISTRATION | SURGEON | CIRCULATING, ASSISTANT | PATIENT HEAD POSITION ANGLE ADJUSTMENT |
| CRANIOTOMY | | ASSISTANT | 2 TO 3 ASSISTANTS | TREPANNING |
| | INCISION | SURGEON | ASSISTANT, SCRUB | RETRACT, MEDICAL TOOL DELIVERY |
| | BLOOD VESSEL SEPARATION | SURGEON | ASSISTANT, SCRUB | RETRACT, MEDICAL TOOL DELIVERY |
| TREATMENT | BLOOD VESSEL SUTURING | SURGEON | ASSISTANT, CIRCULATING, SCRUB | SUTURING, MEDICAL TOOL DELIVERY |
| | AFFECTED PART EXTRACTION | SURGEON | ASSISTANT, SCRUB, CIRCULATING | RETRACT, BIOPSY, MEDICAL TOOL DELIVERY |
| INTRAOPERATIVE DIAGNOSIS | FLUORESCENT OBSERVATION | SURGEON | ANESTHESIOLOGIST, ASSISTANT, SCRUB, CIRCULATING | INTRAVENOUS INJECTION, ROOM LIGHT OFF |
| | DOPPLER BLOOD STREAM CHECK | SURGEON | ASSISTANT, SCRUB, CIRCULATING | BLOOD STREAM OBSERVATION |
| CRANIUM-CLOSING | | ASSISTANT | 2 TO 3 ASSISTANTS | SUTURING |

| PERSONNEL POSITION | MANIPULATION DEVICE | COOPERATION ACTION |
|---|---|---|
| 1. ANESTHESIA INTRODUCTION | ANESTHESIA DEVICE | |
| ALL PERSONNEL AROUND PATIENT | ANESTHESIA DEVICE | |
| ALL DOCTORS AROUND PATIENT | NONE | |
| 2. NAVIGATION | NAVIGATION SYSTEM | |
| 3. CRANIOTOMY | TREPANNING DEVICE | |
| 4. TREATMENT | MICROSCOPE, BIPOLAR, SUCTION DEVICE | SURGEON/ASSISTANT, SURGEON/SCRUB |
| 4. TREATMENT | MICROSCOPE, BIPOLAR, SUCTION DEVICE | SURGEON/ASSISTANT, SURGEON/SCRUB |
| 4. TREATMENT | MICROSCOPE | SURGEON/CIRCULATING/SCRUB |
| 4. TREATMENT | MICROSCOPE, BIPOLAR, SUCTION DEVICE | SURGEON/SCRUB |
| 5. INTRAOPERATIVE DIAGNOSIS | ANESTHESIA DEVICE | SURGEON/ANESTHESIOLOGIST/CIRCULATING/SCRUB |
| 5. INTRAOPERATIVE DIAGNOSIS | ACOUSTIC DOPPLER DEVICE | |
| 6. CRANIUM-CLOSING | NONE | SURGEON/ASSISTANT |

SURGICAL SUPPORT SYSTEM, INFORMATION PROCESSING METHOD, AND INFORMATION PROCESSING APPARATUS

CROSS REFERENCE TO RELATED APPLICATIONS

This application is based on PCT filing PCT/JP2018/025458, filed Jul. 5, 2018, which claims the benefit of Japanese Priority Patent Application JP 2017-142420, filed Jul. 24, 2017, the entire contents of each are incorporated herein by reference.

TECHNICAL FIELD

The present disclosure relates to a surgical support system, an information processing method, and an information processing apparatus.

BACKGROUND ART

In recent years, various techniques have been disclosed as techniques for improving safety of surgery performed at a medical site. For example, a technique of attaching a pedometer and an inclination angle sensor to a nurse and determining whether there is a possibility of an accident occurring on the basis of the number of steps measured by the pedometer and an inclination angle measured by the inclination angle sensor is disclosed (see, for example, PTL 1).

In such a technique, feature data related to a behavior of a nurse is generated on the basis of the number of steps and the inclination angle, and dictionary data for a specific accident is generated on the basis of feature data when a specific accident occurs. Then, after the dictionary data creation, it is determined whether there is a possibility of an accident occurring on the basis of a comparison between the feature data and the dictionary data at a certain time point.

CITATION LIST

Patent Literature

PTL 1: JP 2004-157614A

SUMMARY

Technical Problem

However, in a case in which a sensor is worn by a healthcare professional, the sensor is likely to interfere with an action of the healthcare professional. Particularly, in a case in which an emergency situation or a situation different from a planned situation occurs, or the like, it is likely to be necessary for the healthcare professional to act more quickly than in normal times.

In this regard, it is desirable to provide a technique capable of improving the safety of surgery conducted at a medical site while suppressing a possibility of interfering with a behavior of a healthcare professional.

Solution to Problem

According to an embodiment of the present disclosure, there is provided a surgical support system including: a camera installed in an operating room; and an information processing apparatus including a processing circuitry configured to compare reference data that is related to at least one reference person or reference device in the operating room and that is generated from observation of the operating room, with first feature data related to a first person or a first device extracted from a first image captured by the camera installed in the operating room.

According to an embodiment of the present disclosure, there is provided an information processing method including comparing, by a processor, reference data that is related to a reference person or a reference device in an operating room and that is generated from observation of the operating room, with feature data related to a first person or a first device extracted from the image captured by a camera installed in the operating room, and triggering an alarm warning of a potential issue in the operating room based on a result of the comparing.

According to an embodiment of the present disclosure, there is provided an information processing apparatus including processing circuitry configured to: compare reference data that is related to a reference person or a reference device in an operating room and that is generated from observation of the operating room, with feature data related to a first person or a first device extracted from the image captured by a camera installed in the operating room, and trigger an alarm warning of a potential issue in the operating room based on a result of the comparing.

According to an embodiment of the present disclosure, there is provided a surgical support system including a camera installed in an operating room and an information processing apparatus including processing circuitry configured to compare reference data that is related to at least one person or device in the operating room over time and that is generated from observation of the operating room, with first feature data related to a first person or a first device extracted from a first image captured by the camera installed in the operating room.

Advantageous Effects of Invention

As described above, according to the embodiments of the present disclosure, a technique capable of improving the safety of surgery conducted at a medical site while suppressing a possibility of interfering with a behavior of a healthcare professional is provided. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 13 is a diagram illustrating a correspondence relation of various kinds of information used in an embodiment of the present disclosure.

DESCRIPTION OF EMBODIMENTS

Figure 1:
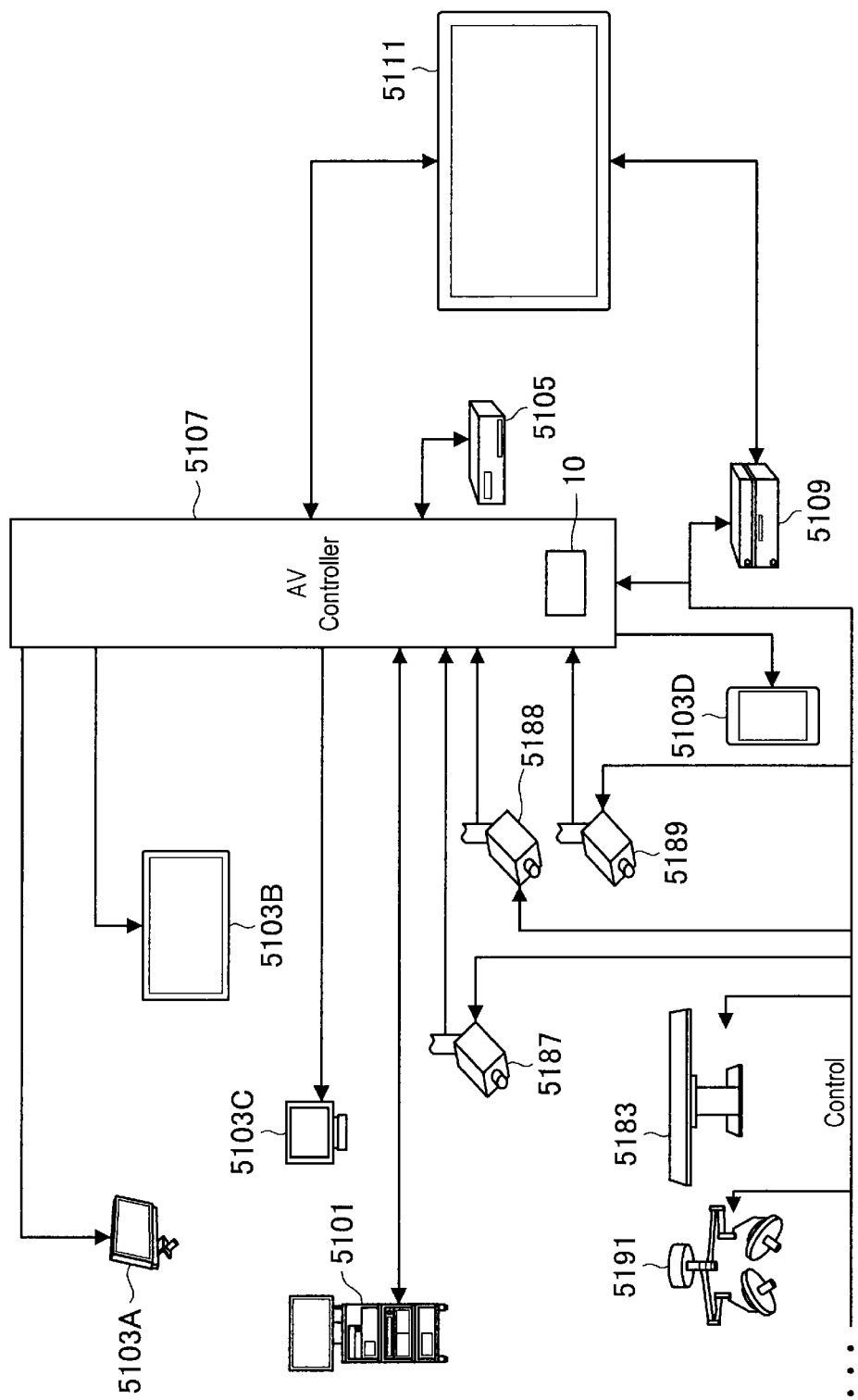
FIG. 1 is a diagram schematically illustrating an overall configuration of an operating room system.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Further, in this specification and the drawings, there are cases in which a plurality of constituent elements having substantially the same or similar functional configuration are distinguished by adding the same reference numeral followed by different numbers. However, in a case in which it is not necessary to particularly distinguish each of a plurality of constituent elements having substantially the same or similar functional configuration, only the same reference numerals are attached. Further, there are cases in which similar constituent elements of different embodiments are distinguished by adding the same reference numeral followed by different letters. However, in a case in which it is not necessary to particularly distinguish each of similar constituent element, only the same reference numerals are attached.

Further, the description will proceed in the following order.

1. System configuration example
2. Overview
3. Details of embodiment
3-1. Work goal setting
3-2. Learning stage
3-3. Operational stage
3-4. Problem search
3-5. Work goal correction
4. Conclusion 1. System Configuration Example First, a configuration example of an example of an information processing system according to an embodiment of the present disclosure will be described with reference to the appended drawings. Various systems are assumed as examples of the information processing system according to an embodiment of the present disclosure. Here, a configuration example of the operating room system will be mainly described as an example of the information processing system according to an embodiment of the present disclosure.

FIG. 1 is a diagram schematically illustrating an overall configuration of an operating room system 5100 to which the technology according to the present disclosure can be applied. Referring to FIG. 1, the operating room system 5100 is configured such that a group of devices installed in an operating room are cooperatively connected to one another via an audiovisual controller (AV controller) 5107 and an operating room control device 5109.

Various devices can be installed in the operating room. As an example, a group 5101 of various kinds of devices for endoscopic surgery, a ceiling camera 5187 which is installed on a ceiling of the operating room and images a hand of a surgeon, an anesthesiologist imaging camera 5188 which is installed on the ceiling of the operating room and images an anesthesiologist, an operating room camera 5189 which is installed on the ceiling of the operating room and images a state of the entire operating room, a plurality of display devices 5103A to 5103D, a recorder 5105, a patient bed 5183, and a lighting 5191 are illustrated in FIG. 1.

Here, the device group 5101 among these devices belongs to an endoscopic surgery system 5113 to be described later and includes an endoscope, a display device that displays an image captured by the endoscope, and the like. Each of the devices belonging to the endoscopic surgery system 5113 is also referred to as a medical device. On the other hand, the display devices 5103A to 5103D, the recorder 5105, the patient bed 5183, and the lighting 5191 are devices installed separately from, for example, the endoscopic surgery system 5113 in the operating room. Each device not belonging to the endoscopic surgery system 5113 is also referred to as a non-medical device. The audiovisual controller 5107 and/or the operating room control device 5109 control the operations of the medical devices and the non-medical devices in cooperation with each other.

The audiovisual controller 5107 controls processes related to image display in the medical devices and the non-medical devices in general. Specifically, the device group 5101, the ceiling camera 5187, and the operating room camera 5189 among the devices included in the operating room system 5100 may be devices having a function of transmitting information to be displayed during surgery (hereinafter also referred to as display information) (hereinafter referred to as transmission source devices). Further, the display devices 5103A to 5103D may be devices from which the display information is output (hereinafter also referred to as output destination devices). Further, the recorder 5105 may be a device corresponding to both the transmission source device and the output destination device. The audiovisual controller 5107 has a function of controlling operations of the transmission source device and the output destination device, acquiring the display information from the transmission source device, and transmitting the display information to the output destination device so that the display information is displayed or recorded. Further, the display information includes various kinds of images captured during the surgery, various kinds of information related to the surgery (for example, body information of a patient, a previous examination result, information related to a surgical form, and the like), and the like.

Specifically, information for an image of a surgery site within a body cavity of the patient imaged by the endoscope can be transmitted from the device group 5101 to the audiovisual controller 5107 as the display information. Further, information for an image of a hand of a surgeon captured by the ceiling camera 5187 can be transmitted from the ceiling camera 5187 as the display information. Further, information for an image illustrating a state of the whole operating room captured by the operating room camera 5189 can be transmitted from the operating room camera 5189 as the display information. Further, in a case in which there is another device having an imaging function in the operating room system 5100, the audiovisual controller 5107 may acquire information for an image captured by another device from another device as the display information.

Alternatively, for example, information for the images which have been captured previously is recorded in the recorder 5105 by the audiovisual controller 5107. The audiovisual controller 5107 can acquire the information for the images which have been captured previously from the recorder 5105 as the display information. Further, various kinds of information related to the surgery may also be recorded in the recorder 5105 in advance.

The audiovisual controller 5107 causes the acquired display information (that is, the image captured during the surgery or various kinds of information related to the surgery) to be displayed on at least one of the display devices 5103A to 5103D which are the output destination devices. In the illustrated example, the display device 5103A is a display device which is installed by suspending it from the ceiling of the operating room, the display device 5103B is a display device which is installed on a wall surface of the operating room, the display device 5103C is a display device which is installed on a desk in the operating room, and the display device 5103D is a mobile device (for example, a tablet personnel computer (PC)) having a display function.

Further, although not illustrated in FIG. 1, the operating room system 5100 may include a device outside the operating room. An external device outside the operating room may be, for example, a server connected to a network constructed inside or outside a hospital, a PC used by a medical staff, a projector installed in a conference room of a hospital, or the like. In a case in which the external device is installed outside the hospital, the audiovisual controller 5107 may cause the display information to be displayed on a display device of another hospital via a teleconference system or the like for remote medical care.

The operating room control device 5109 controls processes other than the processes related to the image display in the non-medical devices in general. For example, the operating room control device 5109 controls driving of the patient bed 5183, the ceiling camera 5187, the operating room camera 5189, and the lighting 5191.

A centralized manipulation panel 5111 is installed in the operating room system 5100, and the user can give an instruction for the image display to the audiovisual controller 5107 via the centralized manipulation panel 5111 and give an instruction for an operation of the non-medical devices to the operating room control device 5109. The centralized manipulation panel 5111 is configured such that a touch panel is installed on the display surface of the display device.

Figure 2:
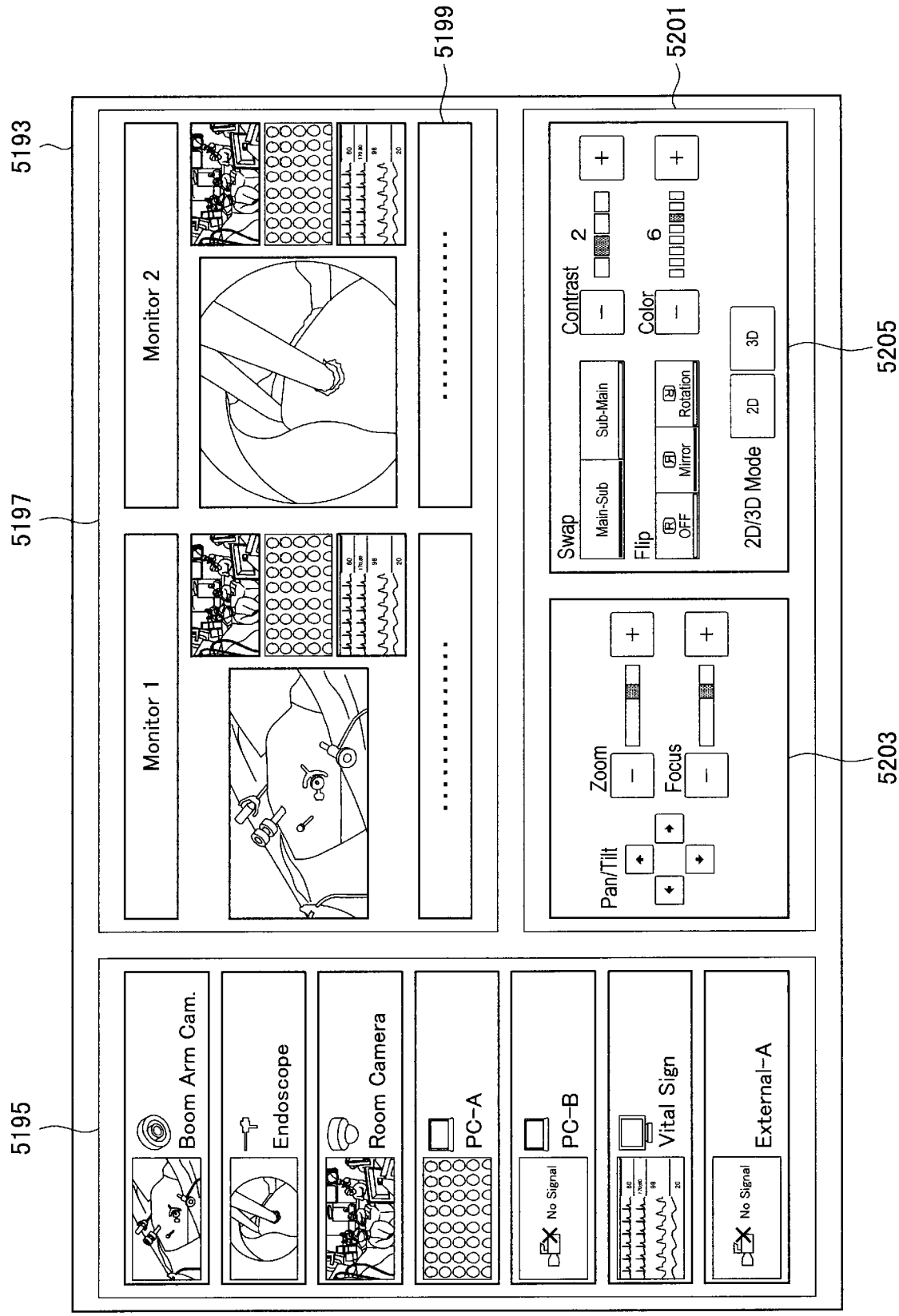
FIG. 2 is a diagram illustrating a display example of a manipulation screen in a centralized manipulation panel.

FIG. 2 is a diagram illustrating a display example of a manipulation screen in the centralized manipulation panel 5111. As an example, a manipulation screen corresponding to a case in which two display devices are installed in the operating room system 5100 as the output destination devices is illustrated in FIG. 2. Referring to FIG. 2, a manipulation screen 5193 includes a transmission source selection area 5195, a preview area 5197, and a control area 5201.

In the transmission source selection area 5195, the transmission source device installed in the operating room system 5100 and a thumbnail screen indicating the display information stored in the transmission source device are displayed in association with each other. The user can select the display information that she or he desires to display on the display device from any one of the transmission source devices displayed in the transmission source selection area 5195.

In the preview area 5197, previews of screens displayed on the two display devices (Monitor 1 and Monitor 2) which are the output destination devices are displayed. In the illustrated example, four images are displayed in a PinP form on one display device. The four images correspond to the display information transmitted from the transmission source devices selected in the transmission source selection area 5195. One of the four images is displayed with a relatively large size as a main image, and the remaining three images are displayed with a relatively small size as sub images. The user can perform switching between the main image and the sub image by appropriately selecting an area in which the four images are displayed. Further, a status display area 5199 is installed below the area in which the four images are displayed, and a status related to surgery (for example, an elapsed time of the surgery, the body information of the patient, or the like) can be appropriately displayed in the area.

A transmission source manipulation area 5203 in which a graphical user interface (GUI) part for performing a manipulation on the transmission source device is displayed and an output destination manipulation area 5205 in which a GUI part for performing a manipulation on the output destination device is displayed are provided in the control area 5201. In the illustrated example, a GUI part for performing various kinds of manipulations (panning, tilting, and zooming) on the camera in the transmission source device with the imaging function is provided in the transmission source manipulation area 5203. The user can manipulate the operation of the camera in the transmission source device by appropriately selecting the GUI parts. Further, although not illustrated, in a case in which the transmission source device selected in the transmission source selection area 5195 is a recorder (that is, in a case in which the image which is previously recorded in the recorder is displayed in the preview area 5197), a GUI part for performing a manipulation such as image reproduction, reproduction stop, rewinding, fast forward, or the like can be provided in the transmission source manipulation area 5203.

Further, a GUI part for performing various kinds of manipulations (swapping, flipping, color adjustment, contrast adjustment, and switching between 2D display and 3D display) with respect to display in the display device which is the output destination device is provided in the output destination manipulation area 5205. The user can manipulate the display in the display device by appropriately selecting these GUI parts.

Further, the manipulation screen displayed on the centralized manipulation panel 5111 is not limited to the illustrated example, and the user may be able to input a manipulation on each device which is installed in the operating room system 5100 and can be controlled by the audiovisual controller 5107 and the operating room control device 5109 through the centralized manipulation panel 5111.

Figure 3:
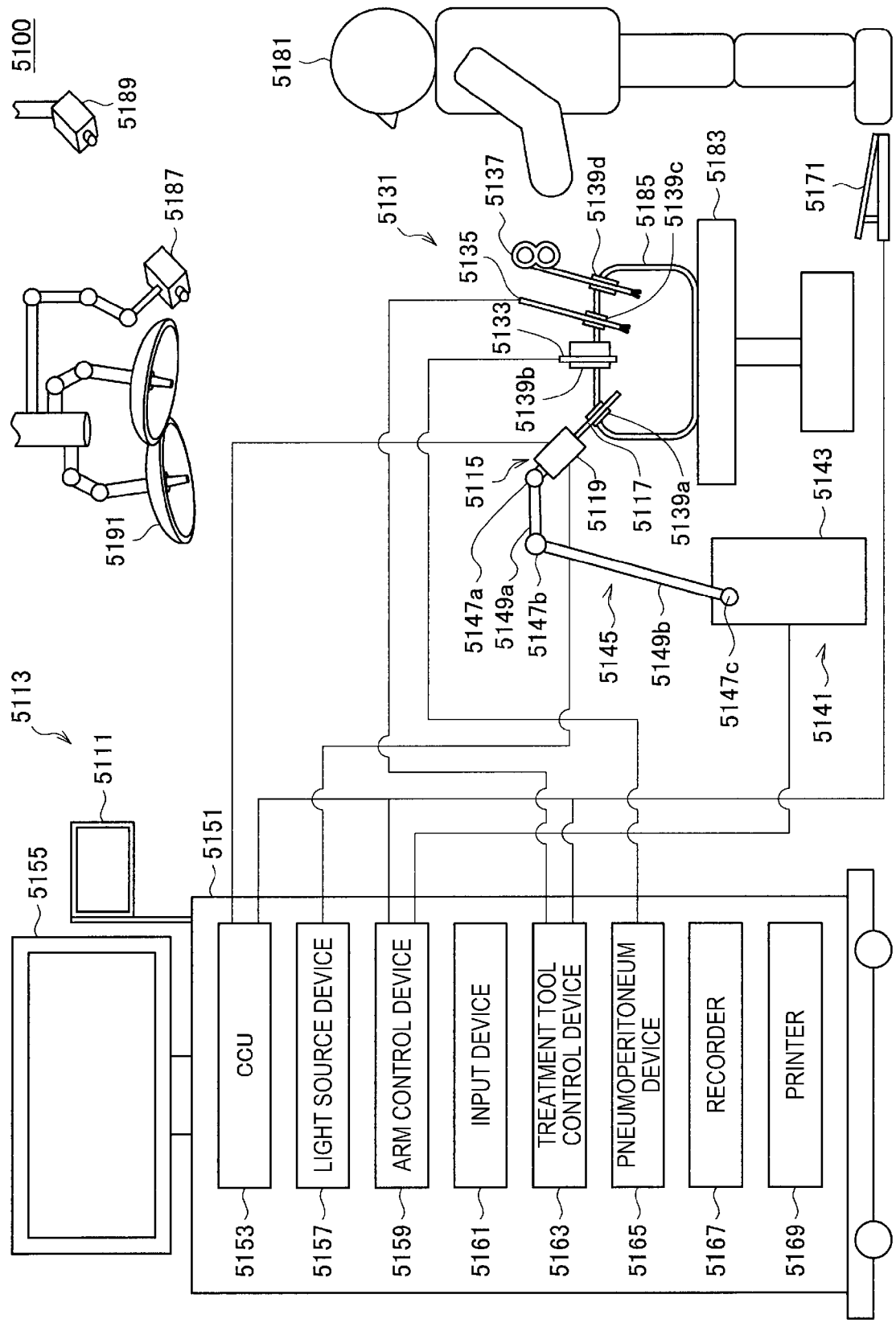
FIG. 3 is a diagram illustrating an example of a state of surgery in which an operating room system is applied.

FIG. 3 is a diagram illustrating an example of a state of surgery to which the operating room system described above is applied. The ceiling camera 5187 and the operating room camera 5189 are installed on the ceiling of the operating room and capable of imaging a hand of a surgeon (physician) 5181 who performs treatment on an affected part of a patient 5185 on the patient bed 5183 and a state of the whole operating room. A magnification adjustment function, a focal length adjustment function, a photographing direction adjustment function, and the like may be provided in the ceiling camera 5187 and the operating room camera 5189. The lighting 5191 is installed on the ceiling of the operating room and illuminates at least the hand of the surgeon 5181. The lighting 5191 may be capable of appropriately adjusting an irradiation light amount, a wavelength (color) of irradiation light, a light irradiation direction, and the like.

As illustrated in FIG. 1, the endoscopic surgery system 5113, the patient bed 5183, the ceiling camera 5187, the operating room camera 5189, and the illumination 5191 are cooperatively connected to one another via the audiovisual controller 5107 and the operating room control device 5109 (not illustrated in FIG. 3). The centralized manipulation panel 5111 is installed in the operating room, and as described above, the user can appropriately manipulate these devices installed in the operating room through the centralized manipulation panel 5111.

Hereinafter, a configuration of the endoscopic surgery system 5113 will be described in detail. As illustrated in the diagram, the endoscopic surgery system 5113 is made up of an endoscope 5115, other surgical instruments 5131, a support arm apparatus 5141 that supports the endoscope 5115, and a cart 5151 on which various devices for endoscopic surgery are provided.

In endoscopic surgery, instead of opening up the abdomen by cutting the abdominal wall, tubular hole-opening tools called trocars 5139a to 5139d are used to puncture the abdominal wall in multiple places. Subsequently, the lens tube 5117 of the endoscope 5115 and other surgical instruments 5131 are inserted into the body cavity of the patient 5185 from the trocars 5139a to 5139d. In the illustrated example, a pneumoperitoneum tube 5133, an energy treatment tool 5135, and forceps 5137 are inserted into the body cavity of the patient 5185 as the other surgical instruments 5131. The energy treatment tool 5135 is a treatment tool that makes incisions into and ablates tissues, or seals blood vessels or the like, with a high-frequency electric current or ultrasonic vibration. However, the surgical instruments 5131 illustrated in the diagram are merely an example, and any of various types of surgical instruments typically used in endoscopic surgery, such as tweezers and retractors, for example, may also be used as the surgical instruments 5131.

An image of the operating site inside the body cavity of the patient 5185 taken by the endoscope 5115 is displayed on a display device 5155. The surgeon 5181 uses the energy treatment tool 5135 and the forceps 5137 to perform treatments, such as excising an affected area, for example, while viewing in real-time the image of the operating site displayed on the display device 5155. Note that, although omitted from the diagram, the pneumoperitoneum tube 5133, the energy treatment tool 5135, and the forceps 5137 are supported by a person such as the surgeon 5181 or an assistant during surgery.

(Support Arm Apparatus)

The support arm apparatus 5141 is provided with an arm unit 5145 that extends from a base unit 5143. In the illustrated example, the arm unit 5145 is made up of joint units 5147a, 5147b, and 5147c, as well as links 5149a and 5149b, and is driven by control commands from the arm control device 5159. The endoscope 5115 is supported by the arm unit 5145, with the position and attitude controlled thereby. With this arrangement, locking of the endoscope 5115 in a stable position may be realized.

(Endoscope)

The endoscope 5115 is made up of a lens tube 5117 having a region of certain length from the front end that is inserted into the body cavity of the patient 5185, and a camera head 5119 connected to the base end of the lens tube 5117. In the example illustrated in the diagram, an endoscope 5115 configured as a so-called rigid scope having a rigid lens tube 5117 is illustrated, but the endoscope 5115 may also be configured as a so-called flexible scope having the flexible lens tube 5117.

On the front end of the lens tube 5117, there is provided an opening into which an objective lens is fitted. A light source device 5157 is connected to the endoscope 5115. Light generated by the light source device 5157 is guided up to the front end of the lens tube 5117 by a light guide extending inside the lens tube 5117, and is radiated through the objective lens towards an observation target inside the body cavity of the patient 5185. Note that the endoscope 5115 may be a forward-viewing scope, an oblique-viewing scope, or a side-viewing scope.

An optical system and an image sensor are provided inside the camera head 5119, and reflected light from the observation target (observation light) is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 5153. Note that the camera head 5119 is provided with a function of adjusting the magnification and the focus distance by appropriately driving the optical system.

Note that, to support stereoscopic vision (3D display) or the like, for example, the camera head 5119 may also be provided with multiple image sensors. In this case, multiple relay optical subsystems are provided inside the lens tube 5117 to guide the observation light to each of the multiple image sensors.

(Various Devices Provided on Cart)

The CCU 5153 is made up of components such as a central processing unit (CPU) and a graphics processing unit (GPU), and centrally controls the operation of the endoscope 5115 and the display device 5155. Specifically, the CCU 5153 subjects an image signal received from the camera head 5119 to various types of image processing for displaying an image based on the image signal, such as development process (demosaicing process), for example. The CCU 5153 provides an image signal that has been subjected to such image processing to the display device 5155. Further, the audiovisual controller 5107 illustrated in FIG. 1 is connected to a CCU 5153. The CCU 5153 also provides an image signal which has undergone image processing to the audiovisual controller 5107. Also, the CCU 5153 transmits a control signal to the camera head 5119 to control the driving thereof. The control signal may include information related to imaging parameters, such as the magnification and focus distance. Information related to imaging parameters may be input via an input device 5161 or may be input via the centralized manipulation panel 5111.

The display device 5155, under control by the CCU 5153, displays an image based on an image signal subjected to image processing by the CCU 5153. In a case in which the endoscope 5115 supports imaging at a high resolution such as 4K (3840 horizontal pixels×2160 vertical pixels) or 8K (7680 horizontal pixels×4320 vertical pixels), and/or supports 3D display, for example, a device compatible with each and capable of high-resolution display and/or capable of 3D display may be used as the display device 5155. In the case in which imaging at a high resolution such as 4K or 8K is supported, a device with a size of 55 inches or more may be used as the display device 5155 to thereby obtain an even deeper sense of immersion. Also, depending on the application, multiple display devices 5155 at different resolutions and sizes may also be provided.

The light source device 5157 is made up of a light source such as a light-emitting diode (LED), for example, and supplies the endoscope 5115 with irradiating light when imaging the operating site.

An arm control device 5159 is made up of a processor such as a CPU, for example, and by operating in accordance with a certain program, controls the driving of the arm unit 5145 of the support arm apparatus 5141 in accordance with a certain control method.

An input device 5161 is an input interface with respect to the endoscopic surgery system 5113. Through the input device 5161, the user is able to input various information and instructions into the endoscopic surgery system 5113. For example, through the input device 5161, the user inputs various information related to surgery, such as physical information about the patient, and information about surgical procedures. As another example, through the input device 5161, the user inputs instructions to drive the arm unit 5145, instructions to change the imaging parameters of imaging by the endoscope 5115 (such as the type of irradiating light, the magnification, and the focus distance), instructions to drive the energy treatment tool 5135, and the like.

The type of the input device 5161 is not limited, and the input device 5161 may be any of various known types of input devices. For example, devices such as a mouse, a keyboard, a touch panel, a switch, a footswitch 5171, and/or a lever may be applied as the input device 5161. In the case in which a touch panel is used as the input device 5161, the touch panel may be provided on the display screen of the display device 5155.

Alternatively, the input device 5161 is a device worn by the user, such as an eyeglasses-style wearable device or a head-mounted display (HMD), for example, and various inputs are performed in accordance with the user's gestures or gaze detected by these devices. Also, the input device 5161 includes a camera able to detect the user's movement, and various inputs are performed in accordance with the user's gestures or gaze detected from a picture imaged by the camera. Furthermore, the input device 5161 includes a microphone able to pick up the user's voice, and various inputs are performed by voice via the microphone. In this way, by configuring the input device 5161 to be capable of accepting the input of various types of information in a noncontact manner, a user belonging to a clean area in particular (for example, the surgeon 5181) becomes able to operate equipment belonging to an unclean area in a noncontact manner. Also, since the user becomes able to operate equipment without taking one's hands away from the tools the user is holding, user convenience is improved.

A treatment tool control device 5163 controls the driving of the energy treatment tool 5135 to cauterize or make incisions into tissue, seal blood vessels, or the like. The pneumoperitoneum device 5165 delivers gas into the body cavity through the pneumoperitoneum tube 5133 to inflate the body cavity of the patient 5185 for the purpose of securing a field of view for the endoscope 5115 and securing a workspace for the surgeon. The recorder 5167 is a device capable of recording various types of information related to surgery. The printer 5169 is a device capable of printing out various types of information related to surgery in various formats, such as text, images, or graphs.

A particularly characteristic configuration in the endoscopic surgery system 5113 will be described below in further detail.

(Support Arm Apparatus)

The support arm apparatus 5141 is equipped with a base unit 5143 which acts as a base, and an arm unit 5145 which extends from the base unit 5143. In the illustrated example, the arm unit 5145 is made up of multiple joint units 5147a, 5147b, and 5147c, as well as multiple links 5149a and 5149b joined by the joint unit 5147b, but in FIG. 3, for the sake of simplicity, the configuration of the arm unit 5145 is illustrated in a simplified manner. In actuality, factors such as the shapes, numbers, and arrangement of the joint units 5147a to 5147c and the links 5149a and 5149b, and the directions of the rotation axes of the joint units 5147a to 5147c may be set appropriately so that the arm unit 5145 has the desired degrees of freedom. For example, the arm unit 5145 preferably may be configured to have six or more degrees of freedom. With this arrangement, it is possible to move the endoscope 5115 freely within the movable range of the arm unit 5145, and thus it becomes possible to insert the lens tube 5117 of the endoscope 5115 into the body cavity of the patient 5185 from a desired direction.

The joint units 5147a to 5147c are provided with an actuator, and the joint units 5147a to 5147c are configured to be rotatable about a certain rotation axis in accordance with the driving of the actuator. By controlling the driving of the actuator with the arm control device 5159, the rotational angle of each of the joint units 5147a to 5147c is controlled, and the driving of the arm unit 5145 is controlled. With this arrangement, control of the position and the attitude of the endoscope 5115 may be realized. At this point, the arm control device 5159 is able to control the driving of the arm unit 5145 with any of various known types of control methods, such as force control or position control.

For example, by having the surgeon 5181 perform appropriate operation input via the input device 5161 (including the footswitch 5171), the driving of the arm unit 5145 may be controlled appropriately by the arm control device 5159 in accordance with the operation input, and the position and the attitude of the endoscope 5115 may be controlled. By such control, after moving the endoscope 5115 on the front end of the arm unit 5145 from an arbitrary position to an arbitrary position, the endoscope 5115 can be supported securely at the new position. Note that the arm unit 5145 may also be operated by what is called a master-slave method. In this case, the arm unit 5145 may be operated remotely by a user via the input device 5161 installed in a location distant from the operating room.

Also, in a case in which force control is applied, the arm control device 5159 may receive external force from the user, and drive the actuator of each of the joint units 5147a to 5147c so that the arm unit 5145 moves smoothly in response to the external force, also known as power assist control. With this arrangement, when the user moves the arm unit 5145 while touching the arm unit 5145 directly, the arm unit 5145 can be moved with comparatively light force. Consequently, it becomes possible to move the endoscope 5115 more intuitively with a simpler operation, and user convenience can be improved.

Herein, in endoscopic surgery, typically the endoscope 5115 has been supported by a doctor called a scopist. In contrast, by using the support arm apparatus 5141, it becomes possible to keep the position of the endoscope 5115 fixed more reliably without manual work, and thus image of the operating site can be obtained consistently, making it possible to perform surgery smoothly.

Note that the arm control device 5159 does not necessarily have to be provided on the cart 5151. Also, the arm control device 5159 does not necessarily have to be a single device. For example, the arm control device 5159 may also be proved respectively in each of the joint units 5147*a* to 5147*c* of the arm unit 5145 of the support arm apparatus 5141, and the multiple arm control devices 5159 may cooperate with each other to realize driving control of the arm unit 5145.

(Light Source Device)

The light source device 5157 supplies the endoscope 5115 with irradiating light when imaging the operating site. The light source device 5157 is made up of a white light source configured by an LED, a laser light source, or a combination of the two, for example. At this point, in the case in which the white light source is configured by a combination of RGB laser light sources, the output intensity and output timing of each color (each wavelength) can be controlled with high precision, and thus the white balance of the captured image can be adjusted with the light source device 5157. Also, in this case, by irradiating the observation target with laser light from each of the RGB laser light sources in a time-division manner, and controlling the driving of the image sensor of the camera head 5119 in synchronization with the irradiation timings, it is also possible to capture images corresponding to R, G, and B, respectively, in a time-division manner. According to such a method, color images can be obtained without providing the image sensor with a color filter.

Also, the driving of the light source device 5157 may also be controlled so as to change the intensity of the light to output every time a certain amount of time elapses. By controlling the driving of the image sensor of the camera head 5119 in synchronization with the timings of changing the light intensity to acquire images in a time-division manner, and compositing the images together, it is possible to generate a high dynamic range image without what are called crushed blacks and blown-out whites.

Additionally, the light source device 5157 may also be configured to be able to supply light in a certain wavelength band corresponding to special imaging. With special imaging, for example, the wavelength dependency of light absorption by tissues of the body is utilized, and light is radiated in a narrow band compared to the irradiating light during normal observation (that is, white light) to thereby image certain tissues, such as blood vessels in the superficial portion of the mucous membrane, at a high contrast, also known as narrow band imaging (NBI). Alternatively, with special imaging, fluorescent observation that obtains an image with fluorescent light by radiating excitation light may also be conducted. With fluorescent observation, it is possible to irradiate a body tissue with excitation light and observe fluorescent light from the body tissue (autofluorescence observation), or locally inject a reagent such as indocyanine green (ICG) into a body tissue while also irradiating that body tissue with excitation light corresponding to the fluorescence wavelength of the reagent to obtain a fluorescent image, or the like. The light source device 5157 may be configured to be able to supply narrow-band light and/or excitation light corresponding to such special imaging.

(Camera Head and CCU)

Figure 4:
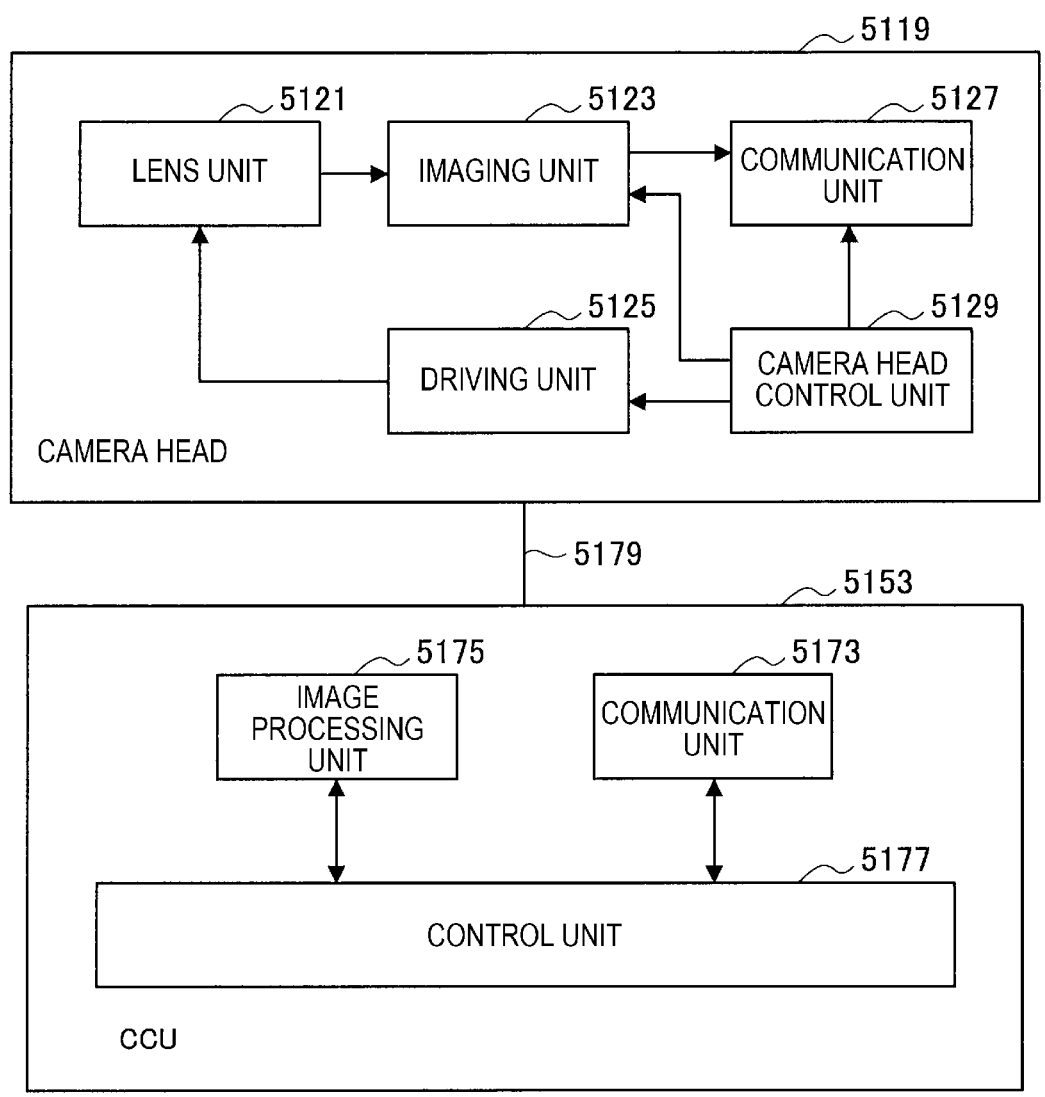
FIG. 4 is a block diagram illustrating an example of a functional configuration of the camera head and the CCU illustrated in FIG. 3.

The functions of the camera head 5119 and the CCU 5153 of the endoscope 5115 will be described in further detail with reference to FIG. 4. FIG. 4 is a block diagram illustrating an example of a functional configuration of the camera head 5119 and the CCU 5153 illustrated in FIG. 3.

Referring to FIG. 4, functionally, the camera head 5119 includes a lens unit 5121, an imaging unit 5123, a driving unit 5125, a communication unit 5127, and a camera head control unit 5129. Also, functionally, the CCU 5153 includes a communication unit 5173, an image processing unit 5175, and a control unit 5177. The camera head 5119 and the CCU 5153 are bidirectionally communicably connected by a transmission cable 5179.

First, a functional configuration of the camera head 5119 will be described. The lens unit 5121 is an optical system provided in the part that connects to the lens tube 5117. Observation light taken in from the front end of the lens tube 5117 is guided up to the camera head 5119, and is incident on the lens unit 5121. The lens unit 5121 is made up of a combination of multiple lenses, including a zoom lens and a focus lens. The optical characteristics of the lens unit 5121 are adjusted to condense observation light onto the photosensitive face of an image sensor in the imaging unit 5123. Also, the zoom lens and the focus lens are configured to be able to move position on the optical axis to adjust the magnification and the focus of the captured image.

The imaging unit 5123 is made up of an image sensor, and is disposed downstream from the lens unit 5121. Observation light passing through the lens unit 5121 is condensed onto the photosensitive face of the image sensor, and by photoelectric conversion, an image signal corresponding to the observed image is generated. The image signal generated by the imaging unit 5123 is provided to the communication unit 5127.

For the image sensor constituting the imaging unit 5123, a complementary metaloxide semiconductor (CMOS) type image sensor having a Bayer array to enable color imaging is used, for example. Note that a sensor capable of capturing high-resolution images of 4K or greater may be used as the image sensor, for example. By obtaining a high-resolution image of the operating site, the surgeon 5181 becomes able to grasp the state of the operating site in greater detail, and proceed with surgery more smoothly.

Also, the image sensor constituting the imaging unit 5123 includes a pair of image sensors for respectively acquiring image signals for the right eye and the left eye corresponding to 3D display. By presenting a 3D display, the surgeon 5181 becomes able to grasp the depth of biological tissue at the operating site more accurately. Note that if the imaging unit 5123 has a multi-chip configuration, the lens unit 5121 likewise is provided with multiple subsystems corresponding to each of the image sensors.

Also, the imaging unit 5123 is not necessarily provided in the camera head 5119. For example, the imaging unit 5123 may also be provided inside the lens tube 5117, directly behind the objective lens.

The driving unit 5125 is made up of actuators, and under control from the camera head control unit 5129, moves the zoom lens and the focus lens of the lens unit 5121 by a certain distance along the optical axis. With this arrangement, the magnification and the focus of the image captured by the imaging unit 5123 may be adjusted appropriately.

The communication unit 5127 is made up of a communication device for transmitting and receiving various information to and from the CCU 5153. The communication unit 5127 transmits an image signal obtained from the imaging unit 5123 as RAW data to the CCU 5153 through the transmission cable 5179. At this point, to display the captured image of the operating site with low latency, the image signal preferably is transmitted by optical communication. This is because during surgery, the surgeon 5181 performs surgery while observing the state of the affected area via the captured image, and thus for safer and more reliable surgery, there is demand for the moving image of the operating site to be displayed as close to real-time as possible. In the case in which optical communication is conducted, the communication unit 5127 is provided with a photoelectric conversion module that converts an electrical signal into an optical signal. The image signal is converted into an optical signal by the photoelectric conversion module, and then transmitted to the CCU 5153 through the transmission cable 5179.

Also, the communication unit 5127 receives from the CCU 5153 a control signal for controlling the driving of the camera head 5119. The control signal includes information related to imaging parameters, such as information specifying the frame rate of the captured image, information specifying the exposure value during imaging, and/or information specifying the magnification and focus of the captured image, for example. The communication unit 5127 provides the received control signal to the camera head control unit 5129. Note that the control signal from the CCU 5153 may also be transmitted by optical communication. In this case, the communication unit 5127 is provided with a photoelectric conversion module that converts an optical signal into an electrical signal, whereby the control signal is converted into an electrical signal by the photoelectric conversion module, and then provided to the camera head control unit 5129.

Note that the above imaging parameters such as the frame rate, the exposure value, the magnification, and the focus are set automatically by the control unit 5177 of the CCU 5153 on the basis of the acquired image signal. In other words, what are called an auto exposure (AE) function, an auto focus (AF) function, and an auto white balance (AWB) function are provided in the endoscope 5115.

The camera head control unit 5129 controls the driving of the camera head 5119 on the basis of a control signal from the CCU 5153 received via the communication unit 5127. For example, the camera head control unit 5129 controls the driving of the image sensor of the imaging unit 5123, on the basis of information specifying the frame rate of the captured image and/or information specifying the exposure during imaging. As another example, the camera head control unit 5129 appropriately moves the zoom lens and the focus lens of the lens unit 5121 via the driving unit 5125, on the basis of information specifying the magnification and the focus of the captured image. Additionally, the camera head control unit 5129 may also be provided with a function of storing information for identifying the lens tube 5117 and the camera head 5119.

Note that by disposing parts of the configuration, such as the lens unit 5121 and the imaging unit 5123, inside a highly airtight and waterproof sealed structure, the camera head 5119 can be made to withstand an autoclaving sterilization process.

Next, a functional configuration of the CCU 5153 will be described. The communication unit 5173 is made up of a communication device for transmitting and receiving various information to and from the camera head 5119. The communication unit 5173 receives an image signal transmitted from the camera head 5119 through the transmission cable 5179. At this point, as described earlier, the image signal preferably may be transmitted by optical communication. In this case, to support optical communication, the communication unit 5173 is provided with a photoelectric conversion module that converts an optical signal into an electrical signal. The communication unit 5173 provides the image signal converted into an electrical signal to the image processing unit 5175.

Also, the communication unit 5173 transmits a control signal for controlling the driving of the camera head 5119 to the camera head 5119. The control signal may also be transmitted by optical communication.

The image processing unit 5175 performs various types of image processing on the image signal made of RAW data transmitted from the camera head 5119. The image processing includes various types of established signal processing, such as a development process, an image quality-improving process (such as a band enhancement process, a super-resolution process, a noise reduction (NR) process, and/or a shake correction process), and/or an enlargement process (digital zoom process), for example. Also, the image processing unit 5175 conducts a wave detection process on the image signal to conduct AE, AF, and AWB.

The image processing unit 5175 is made of a processor such as a CPU or GPU, and by having the processor operate in accordance with a certain program, the image processing and wave detection process described above may be conducted. Note that in the case in which the image processing unit 5175 is made up of multiple GPUs, the image processing unit 5175 appropriately divides up information related to the image signal, and conducts image processing in parallel with the multiple GPUs.

The control unit 5177 performs various controls related to the imaging of the operating site by the endoscope 5115 and the display of a captured image therefrom. For example, the control unit 5177 generates a control signal for controlling the driving of the camera head 5119. At this point, in a case in which imaging parameters are input by the user, the control unit 5177 generates a control signal on the basis of the input by the user. Alternatively, in a case in which the endoscope 5115 is provided with an AE function, an AF function, and an AWB function, the control unit 5177 appropriately computes an optimal exposure value, focus distance, and white balance in accordance with the results of the wave detection process by the image processing unit 5175, and generates a control signal.

In addition, the control unit 5177 causes the display device 5155 to display an image of the operating site on the basis of the image signal subjected to image processing by the image processing unit 5175. At this point, the control unit 5177 uses any of various types of image recognition technology to recognize various objects in the operating site image. For example, by detecting features such as the edge shapes and colors of objects included in the operating site image, the control unit 5177 is able to recognize surgical instruments such as forceps, a specific site of the body, hemorrhaging, mist during usage of the energy treatment tool 5135, and the like. When causing the display device 5155 to display an image of the operating site, the control unit 5177 uses the recognition results to overlay various surgical assistance information onto the image of the operating site. By overlaying and providing the surgeon 5181 with surgical assistance information, it becomes possible to proceed with surgery more safely and reliably.

The transmission cable 5179 that connects the camera head 5119 and the CCU 5153 is an electrical signal cable supporting the communication of electrical signals, optical fiber supporting optical communication, or a composite cable of the above.

At this point, in the illustrated example, communication is conducted in a wired manner using the transmission cable 5179, but communication between the camera head 5119 and the CCU 5153 may also be conducted wirelessly. In the case in which the communication between the two is conducted wirelessly, it is no longer necessary to lay down the transmission cable 5179 inside the operating room, and thus a situation in which the movement of medical staff inside the operating room is impeded by the transmission cable 5179 may be resolved.

The example of the operating room system 5100 to which the technology according to the present disclosure can be applied has been described above. Further, the case in which a medical system to which the operating room system 5100 is applied is the endoscopic surgery system 5113 has been here described as an example, but the configuration of the operating room system 5100 is not limited to this example. For example, the operating room system 5100 may be applied to a flexible endoscope system for inspection or a microscopic surgery system instead of the endoscopic surgery system 5113.

2. Overview

Next, an overview of the technology according to the present disclosure will be described. In recent years, various techniques have been disclosed as techniques for improving safety of surgery performed at a medical site. For example, a technique of attaching a pedometer and an inclination angle sensor to a nurse and determining whether there is a possibility of an accident occurring on the basis of the number of steps measured by the pedometer and an inclination angle measured by the inclination angle sensor is disclosed.

In such a technique, feature data related to a behavior of a nurse is generated on the basis of the number of steps and the inclination angle, and dictionary data (reference data) for a specific accident is generated on the basis of feature data when a specific accident occurs. Then, after the dictionary data creation, it is determined whether there is a possibility of an accident occurring on the basis of a comparison between the feature data and the dictionary data at a certain time point.

However, in a case in which a sensor is worn by a healthcare professional, the sensor is likely to interfere with an action of the healthcare professional. Particularly, in a case in which an emergency situation or a situation different from a planned situation occurs, it is likely to be necessary for the healthcare professional to act more quickly than in normal times.

In this regard, in this specification, a technique capable of improving the safety of surgery conducted at a medical site while suppressing a possibility of interfering with a behavior of a healthcare professional is mainly proposed.

The overview of the technology according to the present disclosure has been described above.

3. Details of Embodiment

Figure 5:
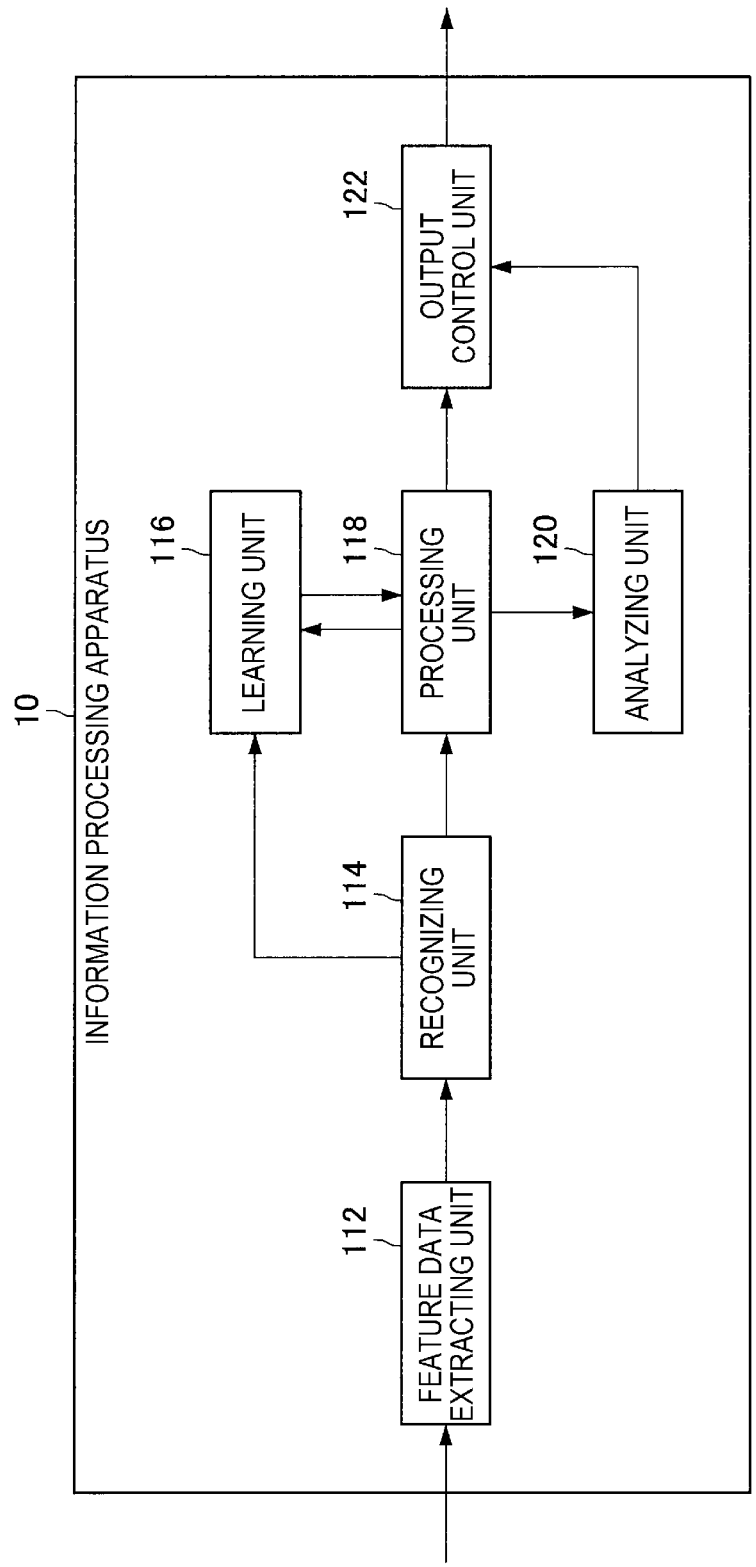
FIG. 5 is a block diagram illustrating a functional configuration example of an information processing apparatus according to an embodiment of the present disclosure.

Next, a functional configuration example of an information processing apparatus according to an embodiment of the present disclosure will be described. FIG. 5 is a block diagram illustrating a functional configuration example of an information processing apparatus according to the embodiment of the present disclosure. As illustrated in FIG. 5, an information processing apparatus 10 according to the embodiment of the present disclosure includes a feature data extracting unit 112, a recognizing unit 114, a learning unit 116, a processing unit 118, an analyzing unit 120, and an output control unit 122. Functions of the functional blocks will be described later in detail.

In the embodiment of the present disclosure, a case in which the information processing apparatus 10 is incorporated into the audiovisual controller 5107 as illustrated in FIG. 1 is assumed. However, a position in which the information processing apparatus 10 is installed is not particularly limited. For example, the information processing apparatus 10 may be installed outside the audiovisual controller 5107.

Figure 6:
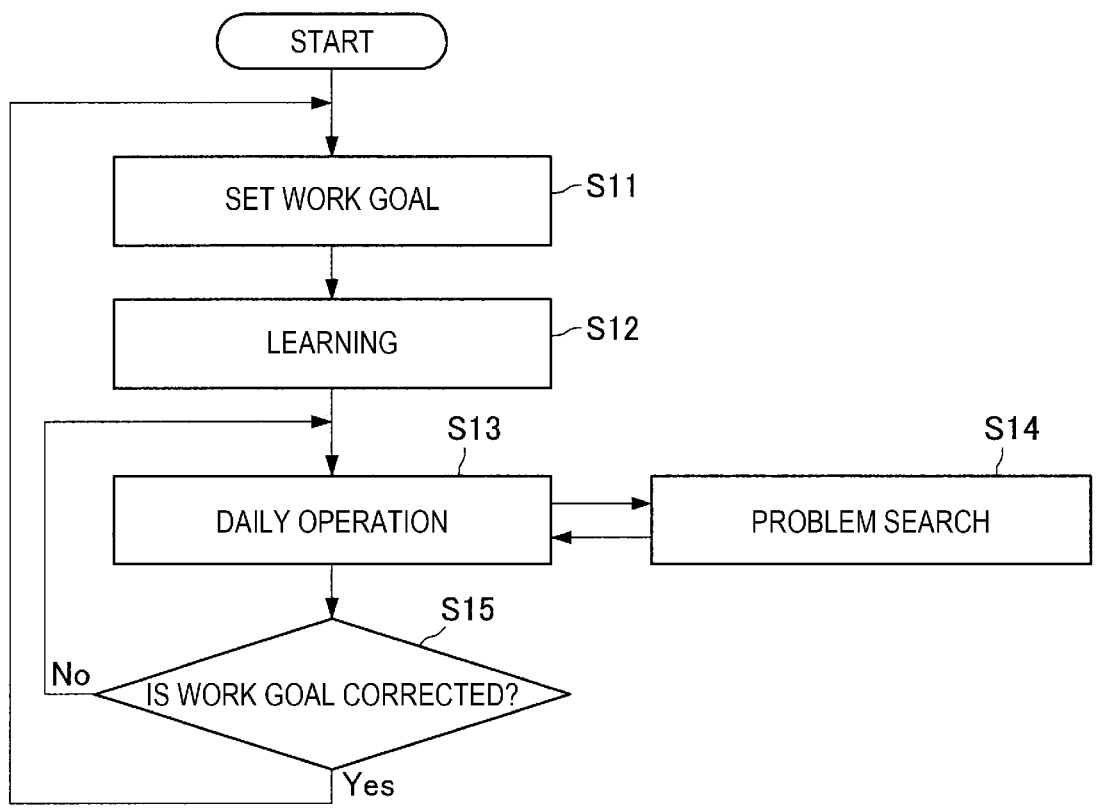
FIG. 6 is a flowchart illustrating an overall operation of an information processing apparatus according to an embodiment of the present disclosure.

FIG. 6 is a flowchart illustrating the overall operation of the information processing apparatus according to the embodiment of the present disclosure. As illustrated in FIG. 6, work goal setting is performed (S11), learning is performed (S12), a daily operation is performed (S13), a problem search is performed on the basis of a daily operation result (S14), and the operation transitions to S13 in a case in which it is unnecessary to correct the work goal ("No" in S15), whereas the operation transitions to S11 in a case in which it is necessary to correct the work goal ("Yes" in S15). These steps will be described in the following sections "3-1. Work goal setting" to "3-5. Work goal correction."

Further, a case in which a neurosurgical operation is performed is assumed mainly as an example of the surgery. However, the technology according to the embodiment of the present disclosure can also be applied to surgery other than the neurosurgical operation. Further, examples of the healthcare professional related to the surgery include a surgeon, an anesthesiologist, an assistant, a circulating nurse (hereinafter also referred to as "circulating"), a scrub nurse (hereinafter also referred to as "scrub"), and a nurse. However, the healthcare professional is not limited to such examples. Further, a person or a healthcare professional is also hereinafter referred to as "personnel." Further, the surgeon is also hereinafter referred to as a "surgeon."

<3-1. Work Goal Setting>

First, the work goal is set. Particularly, the work goal may include a first threshold value, a second threshold value, a third threshold value, and a fourth threshold value to described below. The setting of the work goal may be performed on the basis of an input by any healthcare professional (for example, through the centralized manipulation panel 5111). For example, the setting of the work goal may be performed on the basis of an input by the surgeon (for example, through the centralized manipulation panel 5111).

<3-2. Learning Stage>

The learning stage is set before the operational stage. In the learning stage, the dictionary data to be used in the operational stage is generated from observation of the operating room.

In general, one surgery can be classified into several stages (hereinafter also referred to as "surgery stages"). For example, the neurosurgical operation can be classified into an anesthesia induction stage, a navigation stage, a craniotomy stage, a treatment stage, an intraoperative diagnosis stage, and a cranium-closing stage. At this time, information related to the personnel (for example, personnel positions or the like) and information related to devices (for example, device positions or the like) may change depending on a current surgery stage. As an example, examples of the personnel (reference person) positions and the device (reference device) positions in each surgery stage in the neurosurgical operation will be described.

Figure 7:
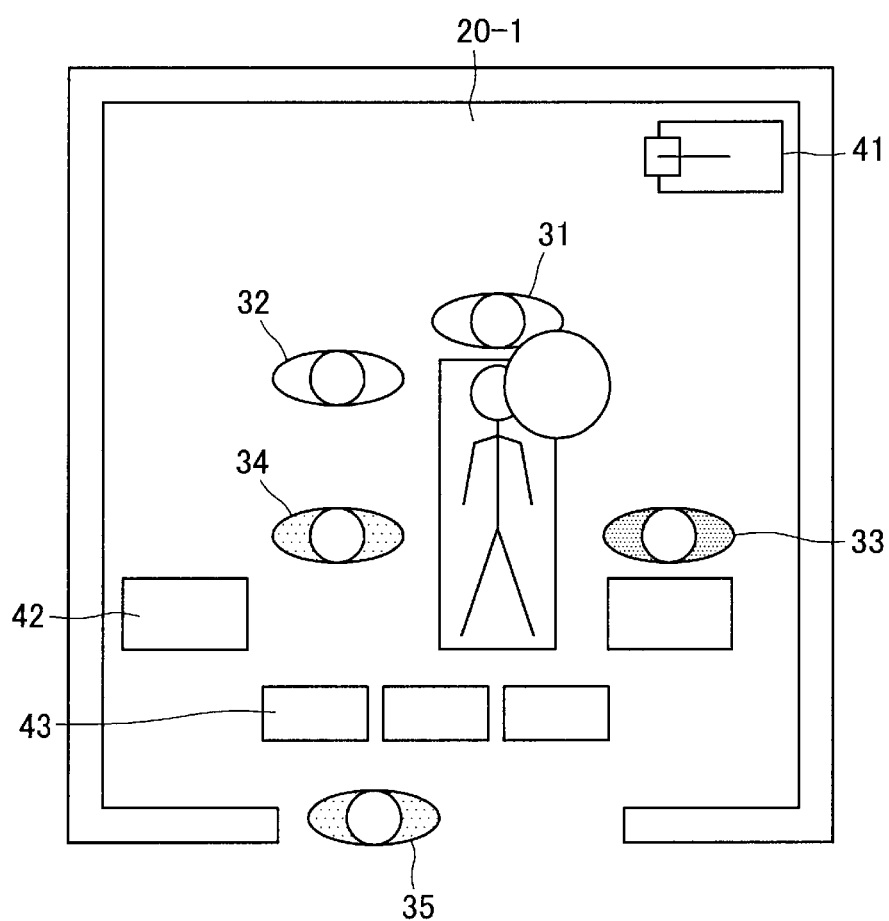
FIG. 7 is a diagram illustrating examples of personnel positions and device positions in an anesthesia induction stage.

FIG. 7 is a diagram illustrating examples of the personnel positions and the device positions in the anesthesia induction stage. Referring to FIG. 7, an operating room 20-1 in the anesthesia induction stage is illustrated. In the anesthesia induction stage, as illustrated in an example in FIG. 7, a surgeon 31, an assistant 32, an anesthesiologist 33, a circulating nurse 34, a scrub nurse 35, a microscope 41, a navigation system 42, a motor evoked potential (MEP) measuring device 43, and an instrument storage 44 are positioned in the operating room 20-1.

Figure 8:
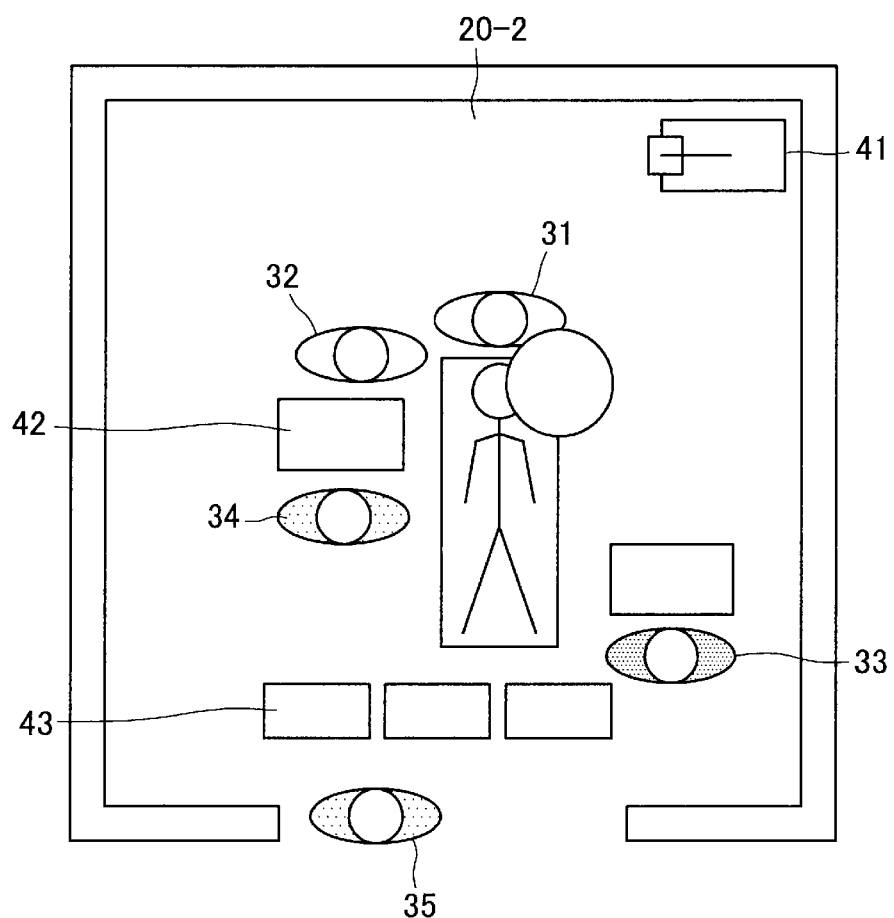
FIG. 8 is a diagram illustrating an example of personnel positions and device positions in a navigation stage.

FIG. 8 is a diagram illustrating an example of the personnel positions and the device positions in the navigation stage. Referring to an operating room 20-2 illustrated in FIG. 8, in the navigation stage, the position of the navigation system 42 changes as compared with that in the anesthesia induction stage.

Figure 9:
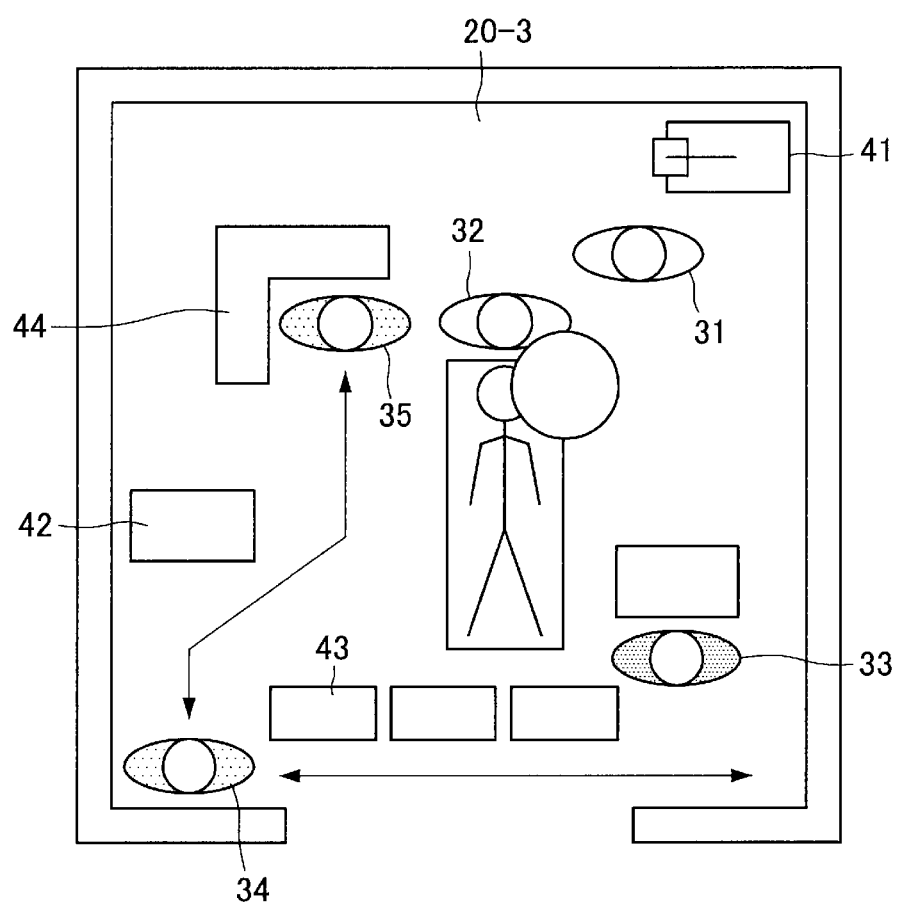
FIG. 9 is a diagram illustrating an example of personnel positions and device positions in a craniotomy stage.

FIG. 9 is a diagram illustrating examples of the personnel positions and the device positions in the craniotomy stage. Referring to an operating room 20-3 illustrated in FIG. 9, in the craniotomy stage, since the craniotomy is performed mainly by the assistant, the positions of the surgeon and the assistant change as compared with those in the navigation stage.

Figure 10:
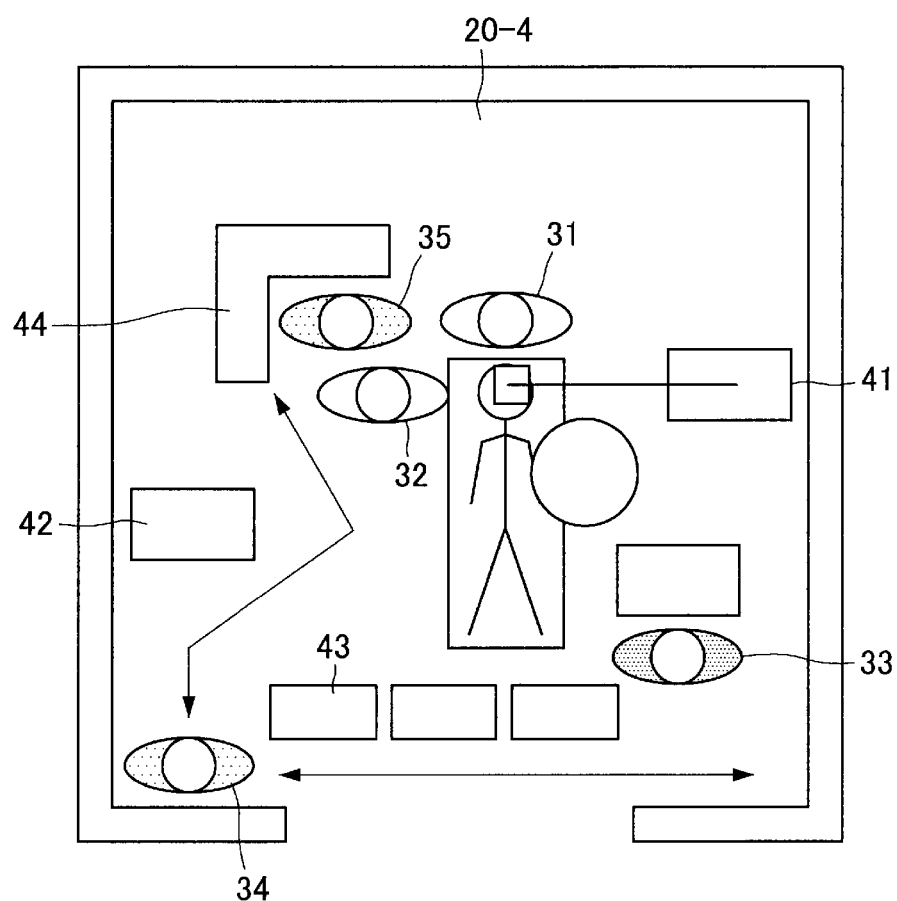
FIG. 10 is a diagram illustrating an example of personnel positions and device positions in a treatment stage.

FIG. 10 is a diagram illustrating an example of the personnel positions and the device positions in the treatment stage. Referring to an operating room 20-4 illustrated in FIG. 10, in the treatment stage, since the treatment is performed mainly by the surgeon, the positions of the surgeon and the assistant change as compared with those in the craniotomy stage. Further, in the treatment stage, since the microscope 41 is used, the position of the microscope 41 changes as compared with that in the craniotomy stage.

Figure 11:
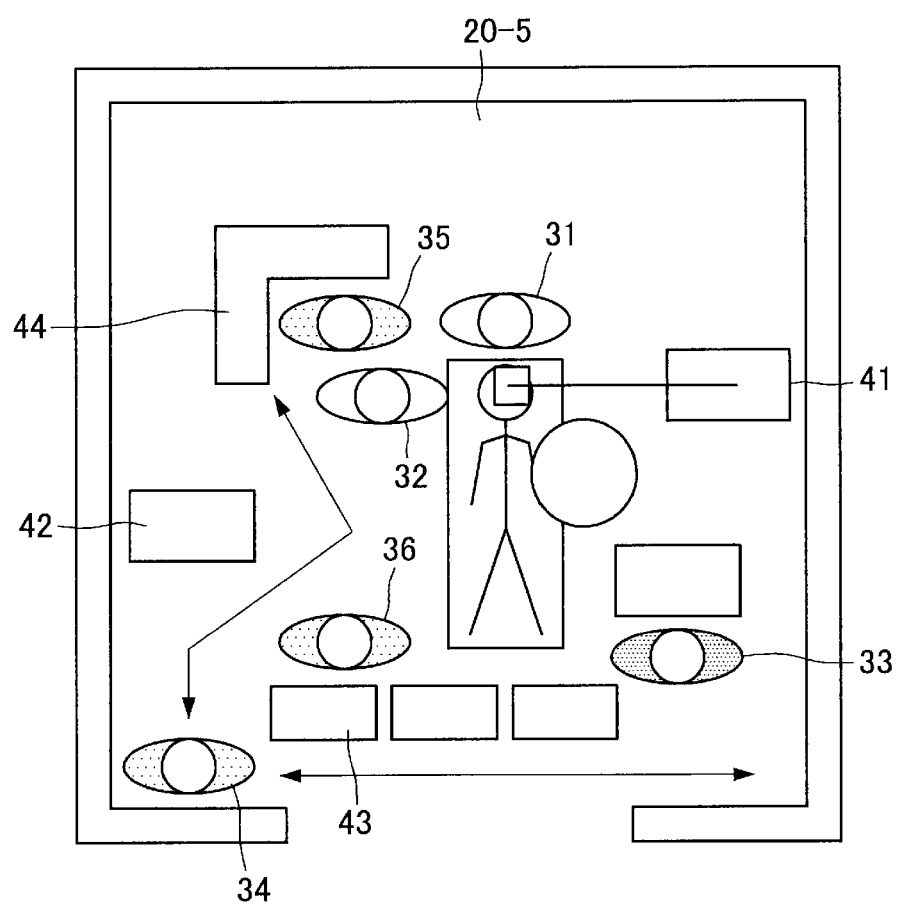
FIG. 11 is a diagram illustrating an example of personnel positions and device positions in an intraoperative diagnosis stage.

FIG. 11 is a diagram illustrating examples of the personnel positions and the device positions in an intraoperative diagnosis stage. Referring to an operating room 20-5 illustrated in FIG. 11, in the intraoperative diagnosis stage, since MEP monitoring using the MEP measuring device 43 is performed, an engineer 36 who manipulates the MEP measuring device 43 is present.

Figure 12:
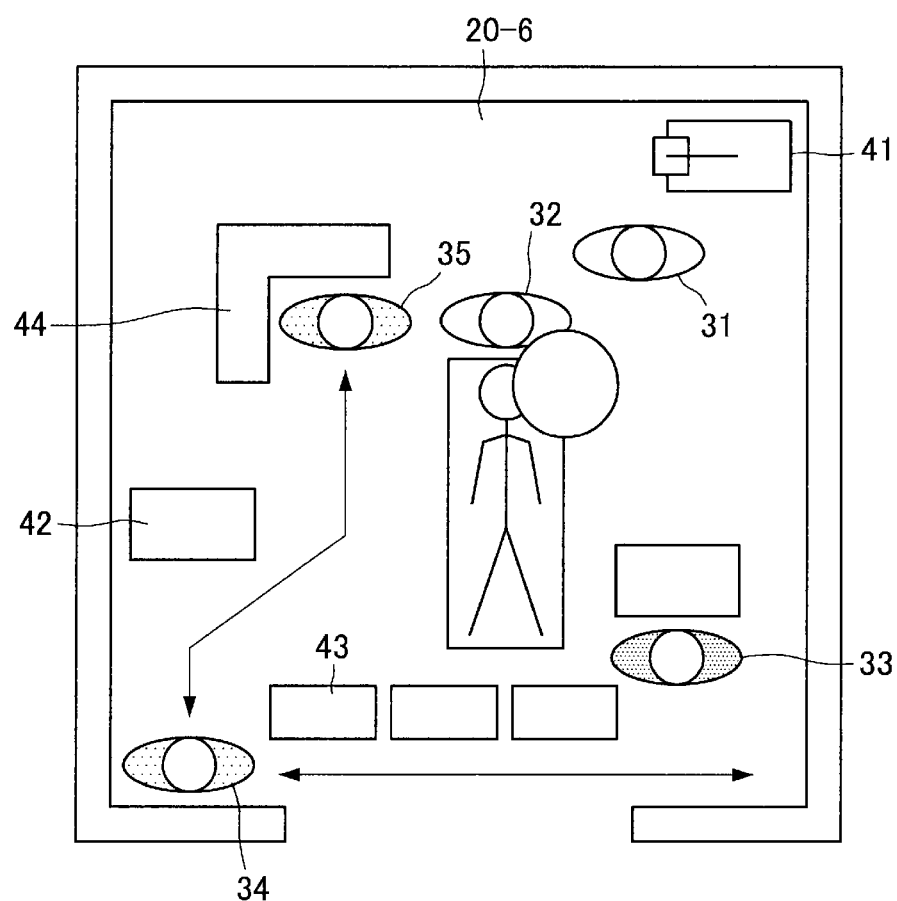
FIG. 12 is a diagram illustrating an example of personnel positions and device positions in a cranium-closing stage.

FIG. 12 is a diagram illustrating examples of the personnel positions and the device positions in the cranium-closing stage. Referring to an operating room 20-6 illustrated in FIG. 12, in the cranium-closing stage, since cranium-closing is performed mainly by the assistant, the positions of the surgeon and the assistant change as compared with those in the intraoperative diagnosis stage. Further, in the cranium-closing stage, since the microscope 41 is not used, the position of microscope 41 changes compared to that in the intraoperative diagnosis stage.

The examples of the personnel positions and the device positions in each surgery stage in the neurosurgical operation have been described. In the learning stage, first, the recognizing unit 114 recognizes the surgery stage. For example, the recognizing unit 114 detects an event and recognizes the surgery stage corresponding to the event. A correspondence relation between the event and the surgery stage may be prepared in advance.

FIG. 13 is a diagram illustrating a correspondence relation of various kinds of information used in the embodiment of the present disclosure. As illustrated in FIG. 13, the surgery stage and the event are associated in advance. For example, the recognizing unit 114 can detect an event from an image captured by the operating room camera 5189 (hereinafter also referred to as an "event detection image"). As described above, the surgery stage corresponding to the event is recognized by detecting the event.

Then, the feature data extracting unit 112 extracts feature data related to a personnel related to the surgery and the device used for the surgery from the image captured by the operating room camera 5189 (hereinafter also referred to as a "learning image"). More specifically, from the learning image, the feature data extracting unit 112 extracts information related to the personnel related to the surgery and information related to the device used for the surgery as an example of the feature data.

The event detection image may be used as the learning image. Alternatively, the learning image may be an image captured by the operating room camera 5189 at a timing having a predetermined relation with a timing at which the event detection image is captured (for example, within a predetermined time range based on a timing at which the event detection image is captured).

Further, a case in which both the information related to the personnel and the information related to the device are used is mainly assumed in the embodiment of the present disclosure. However, only one of the information related to the personnel and the information related to the device may be used.

Further, a case in which information indicating the position of the personnel (hereinafter also referred to as a "personnel position") is used as an example of the information related to the personnel, and information indicating the position of the device (hereinafter also referred to as a "device position") is used as an example of the information related to the device is mainly assumed in the embodiment of the present disclosure. However, the information related to the personnel may be a state of the personnel (for example, a line of sight of the person or the like), and the information related to the device may be a state of the device (for example, whether or not the device is manipulated, whether or not the device is activated, or the like).

A method of extracting the personnel position by the feature data extracting unit 112 is not particularly limited. For example, in a case in which a unique marker is attached to the personnel, the feature data extracting unit 112 can recognize the marker attached to the personnel on the basis of the image captured by the operating room camera 5189 and extracts the personnel position using a marker recognition result.

Further, in common medical institutions, colors of worn clothes may differ depending on types of personnel (roles of the healthcare professional). For example, the surgeon and the assistant are wearing clothes of the same color, but there are cases in which the surgeon and the assistant, the anesthesiologist, the scrub nurse, the circulating nurse, and the engineer are wearing clothes of different colored clothes. Therefore, the feature data extracting unit 112 can recognize the colors of the clothes on the basis of the image captured by the operating room camera 5189 and extract the personnel position using the extraction result of the colors of the clothes instead of the marker recognition result or in addition to the marker recognition result.

Further, there may be cases in which an area in which each type of personnel (each role of the healthcare professional) stays is known in advance. Therefore, the feature data extracting unit 112 can recognize the presence of personnel in the area of each type of personnel (each role of the healthcare professional) and recognize the type of personnel (the role of healthcare professional) staying in the area.

A method of extracting the device position by the feature data extracting unit 112 is not particularly limited. For example, the feature data extracting unit 112 can recognize the device on the basis of the image captured by the operating room camera 5189 and extract the device position using the recognition result for the device. Further, in a case in which a unique marker is attached to the device, the feature data extracting unit 112 can recognize the marker attached to the device on the basis of the image captured by the operating room camera 5189 and extract the device position using the marker recognition result instead of the recognition result for the device or in addition to the recognition result for the device.

Further, the personnel position may include a plurality of positions through which the personnel has passed or may be a center of gravity of a plurality of positions. For example, a motion of the personnel (the healthcare professional) is assumed to differ depending on the type of personnel (the role of healthcare professional). For example, the surgeon or the like often performs a fine motion at a positions which is not changed much in the operating room. In this regard, the position of the personnel (the healthcare professional) who stays at a position which is not changed much such as the surgeon may include a plurality of positions through which the personnel has passed.

On the other hand, the circulating nurse or the like often moves about in the operating room. In this regard, the position of the personnel who often moves around such as the circulating nurse (the healthcare professional) may be a center of gravity of a plurality of positions through which the person has passed. Similarly, the device position may include a plurality of positions through which the device has passed or may be a center of gravity of a plurality of positions.

The learning unit 116 generates the dictionary data related to the personnel and the device in the operating room through learning on the basis of the information related to the personnel and the information related to the device extracted by the feature data extracting unit 112. More specifically, the learning unit 116 generates the dictionary data related to the personnel position and the device position in the operating room through learning on the basis of the personnel position and the device position extracted by the feature data extracting unit 112. The number of personnel positions and the number of device positions used for learning are not limited. For example, each of the number of personnel positions and the number of device positions used for learning may be one, but each of the number of personnel positions and the number of device positions used for learning is preferably two or more in order to improve the accuracy of the dictionary data to be generated.

For example, the learning unit 116 may directly use the personnel position and the device position extracted by the feature data extracting unit 112 for the learning. Alternatively, a case in which the personnel position and the device position extracted from the learning image are displayed (for example, by the centralized manipulation panel 5111), and the personnel position and the device position are corrected (for example, via the centralized manipulation panel 5111) is also assumed. In this case, the learning unit 116 may generate the dictionary data on the basis of the personnel position and the device position which are corrected.

Further, the personnel position and the device position may be corrected by the surgeon but may be corrected by other personnel.

In a case in which the surgery stage is recognized by the recognizing unit 114 as described above, the learning unit 116 generates the dictionary data of the surgery stage recognized by the recognizing unit 114. Alternatively, a case in which the surgery stage recognized by the recognizing unit 114 is displayed (for example, by the centralized manipulation panel 5111), and the surgery stage recognized by the recognizing unit 114 is corrected (for example, via the centralized manipulation panel 5111) is also assumed. In this case, the learning unit 116 generates the dictionary data of the corrected surgery stage.

Referring to FIG. 13, for each surgery stage, doctors mainly related to the surgery are illustrated as "main doctors," and other personnel related to the surgery are illustrated as "other associated personnel." Further, referring to FIG. 13, a "personnel position" serving as an example of the dictionary data is illustrated for each surgery stage. Further, in the "personnel position" illustrated in FIG. 13, "1. Anesthesia introduction" to "6. Cranium-closing" correspond to the personnel positions of the respective surgery stages illustrated in FIGS. 7 to 12. Further, referring to FIG. 13, the device manipulated by the personnel is illustrated as a "manipulation device."

Further, the recognizing unit 114 can recognize cooperation between the personnel from the image captured by the operating room camera 5189 (hereinafter also referred to as a "cooperation recognition image"). In the case in which the cooperation between personnel is recognized from the cooperation recognition image by the recognizing unit 114, the learning unit 116 generates the dictionary data including information related to the cooperation between the personnel.

Referring to FIG. 13, for each surgery stage, the information related to the cooperation serving as an example of the dictionary data is illustrated as a "cooperation action." Further, "A/B" in the "cooperation action" illustrated in FIG. 13 indicates that there is cooperation between A and B. For example, "surgeon/assistant" indicates that there is cooperation between the surgeon and the assistant.

The event detection image or the learning image may be used as the cooperation recognition image. Alternatively, the cooperation recognition image may be an image captured by the operating room camera 5189 at a timing having a predetermined relation with a timing at which the event detection image is captured (within a predetermined time range based on the timing at which the event detection image is imaged).

<3-3. Operational Stage>

Next, the operational stage is set after the learning stage. In the operational stage, it is determined whether or not the progress of the surgery is appropriate with reference to the dictionary data generated over time in the learning stage.

In the operational stage, the recognizing unit 114 recognizes the surgery stage as well. The recognition of the surgery stage in the operational stage is performed, similarly to the recognition of the surgery stage in the learning stage. In other words, the surgery stage recognized in the operational stage may be correctable, similarly to the surgery stage recognized in the learning stage.

Then, the feature data extracting unit 112 extracts the feature data related to the personnel related to the surgery and the device used for the surgery from the image captured by the operating room camera 5189 (hereinafter also referred to as a "comparative image"), similarly to the extraction of the feature data from the learning image. More specifically, the feature data extracting unit 112 extracts the personnel position and the device position from the comparative image as an example of the feature data. Further, the feature data extracted from the comparative image may be correctable, similarly to the feature data extracted from the learning image.

The processing unit 118 compares the dictionary data generated by the learning unit 116 with the feature data extracted from the comparative image. In a case in which the surgery stage is recognized by the recognizing unit 114 as described above, the processing unit 118 compares the dictionary data of the surgery stage recognized by the recognizing unit 114 (the dictionary data related to the personnel position and the device position) with the feature data extracted by the feature data extracting unit 112 (the personnel position and the device position).

In a case in which a difference between the dictionary data of the surgery stage recognized by the recognizing unit 114 (the dictionary data related to the personnel position and the device position) and the feature data extracted by the feature data extracting unit 112 (the personnel position and the device position) exceeds the first threshold value, there is a possibility that the surgery is not performed normally. In this regard, in this case, the output control unit 122 controls an output of first warning information.

Here, an output destination of the first warning information is not limited. For example, in a case in which the first warning information includes the display information, the output destination of the first warning information may be any one of display devices 5103A to 5103D. Alternatively, in a case in which the first warning information includes sound information, the output destination of the first warning information may be a speaker.

Further, for example, in the anesthesia induction stage, the navigation stage, craniotomy stage, and the cranium-closing stage, it is possible to sufficiently determine whether or not the surgery is performed normally on the basis of only the personnel position and the device position.

Further, in a case in which the transition order of the surgery stage differs between the dictionary data and the feature data extracted by the feature data extracting unit 112, there is a possibility that the surgery is not performed normally. Alternatively, in a case in which a difference in a duration of a corresponding surgery stage or an elapsed time up to a corresponding stage between the dictionary data and the feature data extracted by the feature data extracting unit 112 exceeds the threshold value, there is a possibility that the surgery is not performed normally.

In this regard, in this case, the output control unit 122 preferably controls an output of third warning information. An output destination of the third warning information is not limited. For example, in a case in which the third warning information includes the display information, the output destination of the third warning information may be any one of the display devices 5103A to 5103D. Alternatively, in a case in which the third warning information includes the sound information, the output destination of the third warning information may be a speaker.

Further, in a case in which at least one of a plurality of persons who cooperate differs between the dictionary data and the feature data extracted by the feature data extracting unit 112 or in a case in which one of a plurality of persons who cooperate is switched, there is a possibility that the surgery is not performed normally. Further, in a case in which a difference in a duration of cooperation between corresponding personnel or an elapsed time of cooperation between personnel up to a corresponding stage between the dictionary data and the feature data extracted by the feature data extracting unit 112 exceeds the fourth threshold value, there is a possibility that the surgery is not performed normally.

One example of the cooperation between the personnel is cooperation between the surgeon and the anesthesiologist. It is necessary for the anesthesiologist to anticipate a vital change of the patient associated with the treatment behavior by the surgeon and prepare for necessary treatment. For example, in a case in which there is a lack of cooperation between the surgeon and the anesthesiologist (for example, in a case in which the duration of cooperation is too long, in a case in which the elapsed time of cooperation up to a certain stage is too long, or the like), stability and homeostasis (a vital value) of the patient change, and thus it is necessary for the anesthesiologist to suspend the treatment behavior and perform various treatments for stabilizing the vital value.

Another example of the cooperation between the personnel is cooperation among the surgeon, the scrub nurse, and the circulating nurse. The medical device is taken out of a shelf in the operating room or the outside of the operating room by the circulating nurse in accordance with an instruction of the surgeon, passed from circulating nurse to the scrub nurse, and handed from the scrub nurse to the surgeon. For example, in a case in which there is a lack of cooperation between the surgeon and the circulating nurse or the scrub nurse (for example, in a case in which a duration of cooperation is too long, in a case in which an elapsed time of cooperation up to a certain stage is too long, or the like), an arrival of a necessary medical device may be delayed, a standby time may occur, and the homeostasis (the vital value) of the patient may change.

In this regard, in this case, the output control unit 122 controls an output of fourth warning information. An output destination of the fourth warning information is not limited. For example, in a case in which the fourth warning information includes the display information, the output destination of the fourth warning information may be any one of display devices 5103A to 5103D. Alternatively, in a case in which the fourth warning information includes the sound information, the output destination of the fourth warning information may be a speaker.

Further, for example, in the treatment stage, it is determined whether or not the surgery is performed normally in view of the cooperation between the surgeon and the assistant during the treatment, the cooperation between the surgeon and the scrub for surgery tool switching, and the cooperation among the surgeon, the scrub, and the circulating nurse such as delivery of the surgery tool or biopsy submission of excised tissue in addition to the personnel position and the device position. Further, for example, in the intraoperative diagnosis stage, it is preferable to determine whether or not the surgery is performed normally in view of the cooperation between the surgeon and the anesthesiologist in addition to the personnel position and the device position.

Further, the evaluation of the motion of the anesthesiologist can be performed by various techniques. For example, as described above, it may be determined whether or not the position of the anesthesiologist serving as an example of the personnel is normal on the basis of the image captured by the operating room camera 5189. On the other hand, there is the anesthesiologist imaging camera 5188 which images the anesthesiologist. The state of the anesthesiologist (such as the line of sight of the anesthesiologist) may be acquired on the basis of the image captured by the anesthesiologist imaging camera 5188, and it may be determined whether or not the surgery is performed normally on the basis of the state of the anesthesiologist.

For example, the state of the anesthesiologist can be a state such as whether or not the anesthesiologist is looking at a patient, whether or not the anesthesiologist is looking at the surgeon, whether or not the anesthesiologist is looking at the vital screen of the patient. For example, in a case in which the state of the anesthesiologist indicates that the anesthesiologist is looking at the surgeon, the cooperation may be determined to be performed between the surgeon and the anesthesiologist. As described above, it may be determined whether or not the cooperation is performed between the surgeon and the anesthesiologist on the basis of the state of the anesthesiologist.

As described above, in the operational stage, the output control unit 122 controls the output of the warning information (for example, the first warning information, the second warning information, the third warning information, and the fourth warning information). Accordingly, the healthcare professional who perceived the warning information can take measures to prevent the patient from falling into a dangerous state.

Figure 14:
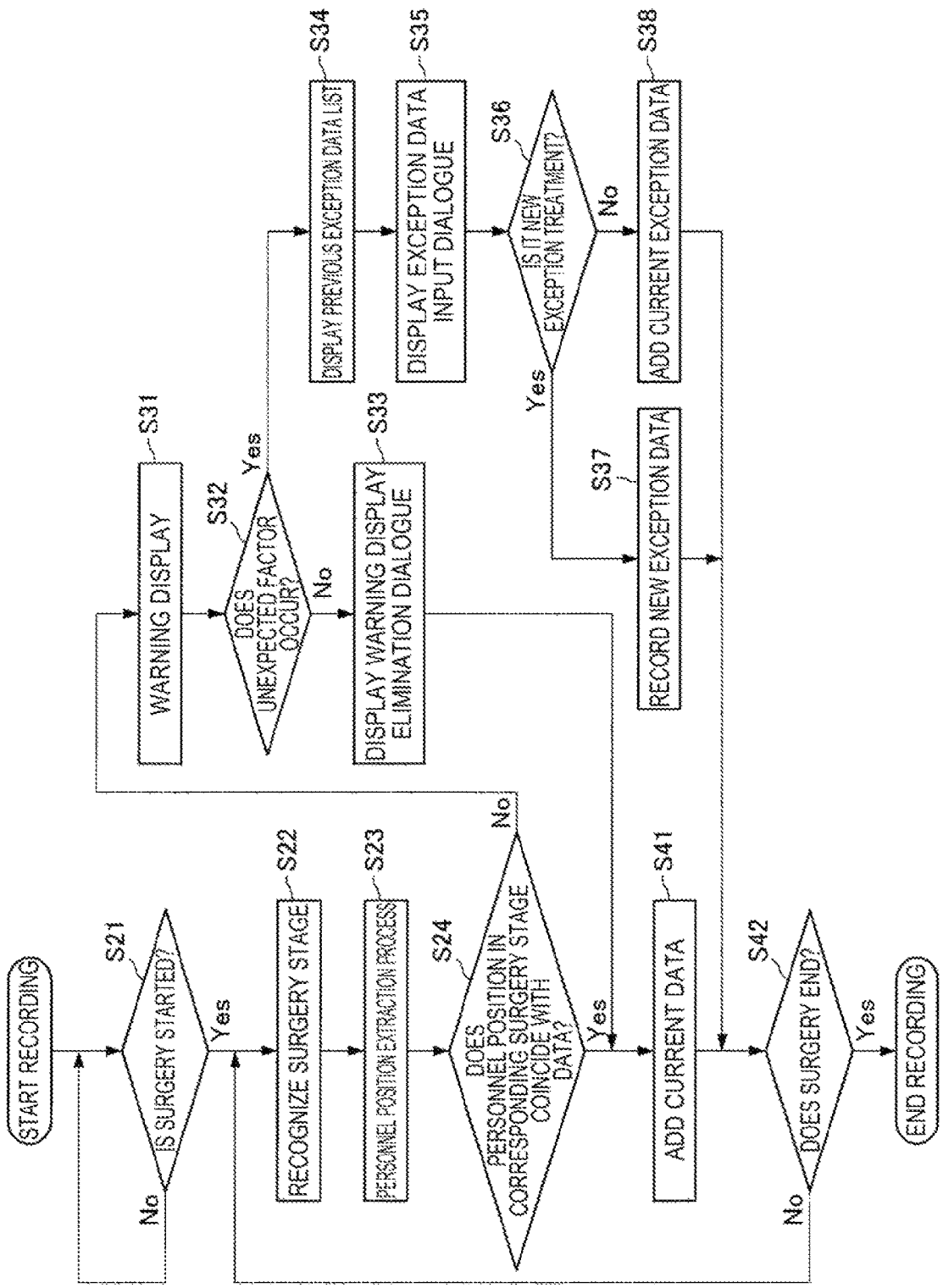
FIG. 14 is a flowchart illustrating an operation example of a warning display based on personnel positions in an operational stage.

FIG. 14 is a flowchart illustrating an example of an operation of the warning display based on the personnel position in the operational stage. As illustrated in FIG. 14, recording of the image captured by the operating room camera 5189 is started. Further, in a case in which the surgery is not started ("No" in S21), the recognizing unit 114 causes the operation to transition to S21. On the other hand, in a case in which the surgery is started ("Yes" in S21), the recognizing unit 114 recognizes the surgery stage (S22).

Further, a method of determining whether or not the surgery is started or not through the recognizing unit 114 is not particularly limited. As an example, the recognizing unit 114 may determine that the surgery is started in a case in which an initial surgery stage is recognized.

Then, the feature data extracting unit 112 extracts the personnel position from the image captured by the operating room camera 5189 (S23). Then, the processing unit 118 determines whether or not the personnel position coincides with the data (dictionary data) in the corresponding surgery stage (the surgery stage recognized by the recognizing unit 114) (S24). In a case in which it is determined that the personnel position does not coincide with the data (dictionary data) in the corresponding surgery stage ("No" in S24), the output control unit 122 controls the warning display (S31). Further, sound output indicating a warning may be controlled instead of the warning display.

Further, in a case in which an unexpected factor does not occurs ("No" in S32), the output control unit 122 controls display of a warning display elimination dialogue (S33). In a case in which a manipulation indicating the elimination of the warning display is input in the warning display elimination dialogue, the output control unit 122 causes the operation to transit to S41. Further, the manipulation indicating the elimination of the warning display may be input by the surgeon, the nurse, or the like (via the centralized manipulation panel 5111 or another input device).

On the other hand, in a case in which an unexpected factor occurs ("Yes" in S32), the output control unit 122 controls display of a previous exception data list (S34) and controls display of an exception data input dialogue (S35). Further, it may be input whether or not an unexpected factors occurs by the surgeon, the nurse, or the like (via the centralized manipulation panel 5111 or another input device).

In a case in which a manipulation indicating that surgery currently being performed is a new exceptional treatment is inputted ("Yes" in S36), the output control unit 122 registers data related to the surgery currently being performed in previous exception data as current exception data (S37), and causes the operation to transition to S42. On the other hand, in a case in which a manipulation indicating that the surgery currently being performed is not a new exceptional treatment is input ("No" in S36), data related to the surgery currently being performed is added to the previous exception data as current exception data (S38) and causes the operation to transit to S42.

Further, the new exception treatment may be any treatment. For example, it is assumed that old-style surgery is performed exceptionally or the like, but in this case, the old-style surgery may be dealt as the new exceptional treatment. It is assumed that new-style surgery is performed in principle or the like, but in this case, the new-style surgery may be dealt as treatment other than the new exception treatment. Further, it may be input whether or not the current surgery is a new exceptional treatment by the surgeon, the nurse, or the like (via the centralized manipulation panel 5111 or another input device).

In a case in which the output control unit 122 determines that the personnel position coincides with the data (dictionary data) in the corresponding surgery stage ("Yes" in S24), the output control unit 122 adds the current data (the data related to the surgery currently being performed) to the previous data (S41). Further, in a case in which the surgery does not end ("No" in S42), the operation transitions to S22. On the other hand, in a case in which the surgery ends ("Yes" in S42), the recording of the image captured by the operating room camera 5189 ends.

Figure 15:
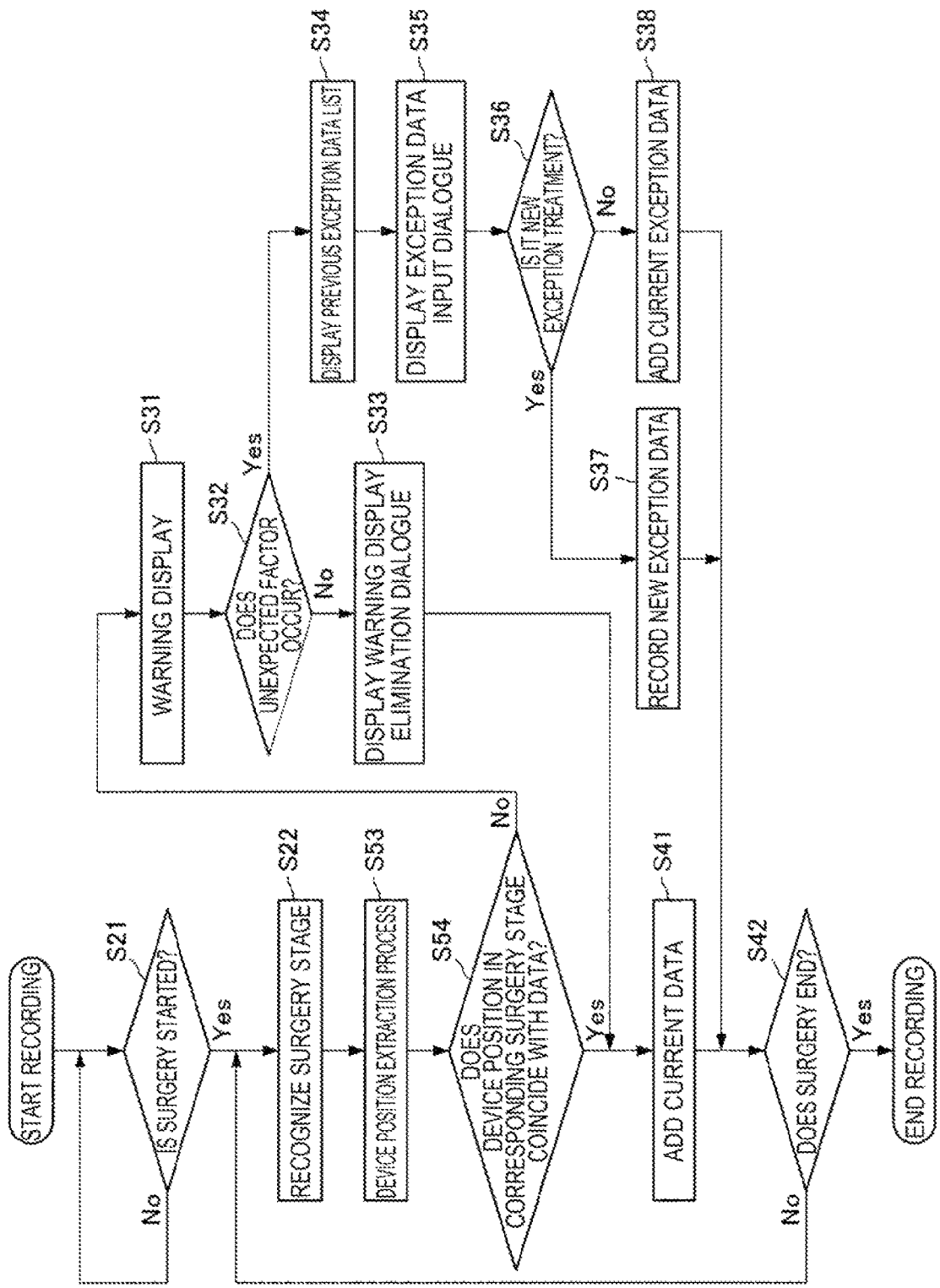
FIG. 15 is a flowchart illustrating an operation example of a warning display based on device positions in an operational stage.

FIG. 15 is a flowchart illustrating an operation example of the warning display based on the device position in the operational stage. For example, the operation of the warning display based on the device position in the operational stage may be performed in parallel with the operation of the warning display based on the personnel position in the operational stage illustrated in FIG. 14. Here, description of the same operation example as the operation example illustrated in FIG. 14 among the operation examples illustrated in FIG. 15 will be omitted, and an operation example different from the operation example illustrated in FIG. 14 will mainly be described.

As illustrated in FIG. 15, in a case in which the surgery stage is recognized by the recognizing unit 114 (S22), the feature data extracting unit 112 performs a process of extracting the device position from the image captured by the operating room camera 5189 (S53). Then, the processing unit 118 determines whether or not the device position coincides with the data (dictionary data) in the corresponding surgery stage (S54). In a case in which it is determined that the device position does not coincide with the data (dictionary data) in the corresponding surgery stage ("No" in S54), the output control unit 122 controls the warning display (S31).

On the other hand, in a case in which it is determined that the device position coincides with the data (dictionary data) in the corresponding surgery stage ("Yes" in S54), the output control unit 122 adds the current data (the data related to the surgery currently being performed) to the previous data (S41).

<3-4. Problem Search>

Further, it can be determined whether or not there is no problem in the surgery depending on how far prognostic information after the surgery is away from standard data.

Here, the prognostic information may include any information. For example, the prognostic information may include at least one of a hospitalization period of the patient, stability of a symptom of the patient after the surgery, and information indicating the state of the patient after the surgery. For example, the prognostic information is input in association with the comparative image by the surgeon (via the centralized manipulation panel 5111).

The processing unit 118 determines how far the prognostic information after the surgery is away from the standard data. In other words, the processing unit 118 compares the prognostic information associated with the comparative image with preset standard data. The output control unit 122 controls an output of the second warning information in a case in which a difference between the prognostic information and the standard data exceeds the second threshold value. An output destination of the second warning information is not limited. For example, in a case in which the second warning information includes the display information, the output destination of the second warning information may be any one of display devices 5103A to 5103D. Alternatively, in a case in which the second warning information includes the sound information, the output destination of the second warning information may be a speaker.

Further, since the prognostic information after the surgery is assumed to differ depending on the type of surgery (for example, the neurosurgical operation, the cardiac surgery, or the like), it is preferable to set the standard data in accordance with the type of surgery. Therefore, it is preferable that the output control unit 122 control the output of the second warning information in a case in which the difference between the prognostic information and the standard data acquired in accordance with the type of the surgery performed in the operating room exceeds the second threshold value. The type of surgery may be recorded in advance (for example, in the recorder 5105).

In a case in which the difference from the standard data exceeds the second threshold value, and a plurality of pieces of identical or similar prognostic information are extracted, the analyzing unit 120 may acquire the information related to the cooperation between the personnel, the information related to the position or the action of each personnel, a duration of the surgery stage, or the elapsed time up to a predetermined stage in the surgery stage which is associated with each of the plurality of pieces of prognostic information.

Then, the analyzing unit 120 may analyze the information related to the cooperation between the personnel, the information related to the position or the action of each personnel, a duration of the surgery stage, or the elapsed time up to a predetermined stage in the surrey stage which is acquired as described above. With such analysis, it is possible to understand the tendency of surgery having a problem (it is possible to detect a risk action of the healthcare professional to be improved).

<3-5. Work Goal Correction>

Then, in a case in which it is necessary to correct the work goal, the work goal is corrected. Particularly, the work goal which can be corrected may include the first threshold value, the second threshold value, the third threshold value, and the fourth threshold value as described above. The correction of the work goal may be performed on the basis of an input of any one healthcare professional (or example, via the centralized manipulation panel 5111). For example, the correction of the work goal may be performed on the basis of an input by the surgeon (for example, via the centralized manipulation panel 5111).

The functional configuration example of the information processing apparatus 10 according to the embodiment of the present disclosure has been described above.

4. Conclusion

As described above, according to the embodiment of the present disclosure, the information processing apparatus 10 including the processing unit 118 that compares dictionary data related to a person or a device in the operating room obtained by learning with first feature data related to the person or the device extracted from a first image captured by the camera installed in the operating room is provided. According to such a configuration, it is possible to improve the safety of the surgery performed at a medical site while suppressing a possibility of interfering with a behavior of the healthcare professional.

It should be understood by those skilled in the art that various modifications, combinations, sub-combinations and alterations may occur depending on design requirements and other factors insofar as they are within the scope of the appended claims or the equivalents thereof.

For example, the example in which the personnel position is extracted from the image captured by the operating room camera 5189, and it is determined whether or not the surgery is performed normally on the basis of the extracted personnel position has been described above. The example in which the state of the anesthesiologist is extracted from the image captured by the anesthesiologist imaging camera 5188, and it is determined whether or not the surgery is performed normally on the basis of the state of the extracted anesthesiologist has been described above. However, it may be determined whether or not the surgery is performed normally on the basis of sensing data (for example, sound information detected by a microphone, measurement data detected by various kinds of medical devices, or the like) instead of the image.

Further, for example, it is also possible to generate a program causing hardware such as a CPU, a ROM and a RAM installed in a computer to perform functions equivalent to the functions provided by the information processing apparatus 10. Further, it is possible to provide a computer-readable recording medium in which the program is recorded.

Further, the effects described in this specification are merely illustrative or exemplified effects, and are not limitative. That is, with or in the place of the above effects, the technology according to an embodiment of the present disclosure may achieve other effects that are clear to those skilled in the art from the description of this specification.

Additionally, the present technology may also be configured as below.

(1)

A surgery system, including:
    a camera installed in an operating room; and
    an information processing apparatus including a processing unit configured to compare dictionary data that is related to a person or a device in the operating room and that is obtained by learning, with first feature data related to a person or a device extracted from a first image captured by the camera installed in the operating room.

(2)

The surgery system according to (1), in which the information processing apparatus includes an output control unit configured to control an output of first warning information in a case in which a difference between the dictionary data and the first feature data exceeds a first threshold value.

(3)

The surgery system according to (1), in which the processing unit compares standard data with prognostic information associated with the first image.

(4)

The surgery system according to (3), in which the information processing apparatus includes an output control unit configured to control an output of second warning information in a case in which a difference between the prognostic information and the standard data exceeds a second threshold value.

(5)

The surgery system according to (4), in which, in a case in which the difference between the prognostic information and the standard data acquired in accordance with a type of surgery performed in the operating room exceeds the second threshold value, the output control unit controls the output of the second warning information.

(6)

The surgery system according to (3), in which the information processing apparatus includes an analyzing unit configured to acquire information related to cooperation between persons, information related to a position or a motion of each person, a duration of a surgery stage, or an elapsed time up to a predetermined stage in a surgery stage, the information, the duration, and the elapsed time being associated with each of a plurality of pieces of prognostic information, in a case in which a difference from the standard data exceeds the second threshold value and the plurality of pieces of identical or similar prognostic information are extracted.

(7)

The surgery system according to any one of (3) to (6), in which the prognostic information includes at least one of a hospitalization period of a patient, stability of a symptom of the patient after surgery, and information indicating a state of the patient after the surgery.

(8)

The surgery system according to any one of (1) to (7), in which the processing unit compares dictionary data that is related to a position of a person or a device in the operating room and that is obtained by learning, with first feature data indicating a position of a person or a device extracted from the first image.

(9)

The surgery system according to (8), in which the first feature data includes a plurality of positions through which the person or the device has passed or a center of gravity of the plurality of positions.

(10)

The surgery system according to any one of (1) to (9), in which, in a case in which a surgery stage is recognized from the first image or an image captured at a timing having a predetermined relation with a timing at which the first image is captured, the processing unit compares dictionary data of the surgery stage with the first feature data.

(11)

The surgery system according to (10), in which the surgery stage is recognized by detection of an event corresponding to the surgery stage.

(12)

The surgery system according to any one of (1) to (11), in which, in a case in which second feature data related to a person or a device extracted from a second image is corrected, the dictionary data is generated on a basis of the correction.

(13)

The surgery system according to (12), in which, in a case in which a surgery stage is recognized from the second image or an image captured at a timing having a predetermined relation with a timing at which the second image is captured, the dictionary data is generated as dictionary data of the surgery stage.

(14)

The surgery system according to (13), in which the information processing apparatus includes an output control unit configured to control an output of third warning information in a case in which a transition order of the surgery stage differs between the dictionary data and the first feature data or in a case in which a difference in a duration of a corresponding surgery stage or an elapsed time up to a corresponding stage exceeds a third threshold value.

(15)

The surgery system according to (1), in which the dictionary data is generated such that the dictionary data includes information related to cooperation between persons in a case in which the cooperation between the persons is recognized from a third image.

(16)

The surgery system according to (15), in which the information processing apparatus includes an output control unit configured to control an output of fourth warning information in a case in which at least one of a plurality of persons who cooperate with each other differs between the dictionary data and the first feature data, in a case in which one of a plurality of persons who cooperate with each other is switched, or in a case in which a difference in a duration of cooperation between corresponding persons or an elapsed time of cooperation between persons up to a corresponding stage exceeds a fourth threshold value.

(17)

The surgery system according to any one of (1) to (16), in which the information processing apparatus includes a learning unit configured to generate the dictionary data related to the person or the device in the operating room by learning.

(18)

The surgery system according to any one of (1) to (17), in which the information processing apparatus includes a feature data extracting unit configured to extract the first feature data from the first image.

(19)

An information processing method, including:
  comparing, by a processor, dictionary data that is related to a person or a device in an operating room and that is obtained by learning, with feature data related to a person or a device extracted from an image captured by a camera installed in the operating room.

(20)

An information processing apparatus, including:
  a processing unit configured to compare dictionary data that is related to a person or a device in an operating room and that is obtained by learning, with feature data related to a person or a device extracted from an image captured by a camera.

(21)

A surgical support system, including:
  a camera installed in an operating room; and
  an information processing apparatus including processing circuitry configured to compare reference data that is related to at least one reference person or reference device in the operating room and that is generated from observation of the operating room, with first feature data related to a first person or a first device extracted from a first image captured by the camera installed in the operating room.

(22)
The surgical support system according to (21), wherein the processing circuitry is further configured to control an output of first warning information when a difference between the reference data and the first feature data exceeds a first threshold value.

(23)
The surgical support system according to (21), wherein the processing circuitry is further configured to compare standard data with prognostic information associated with the first image.

(24)
The surgical support system according to (23), wherein the processing circuitry is further configured to control an output of second warning information when a difference between the prognostic information and the standard data exceeds a second threshold value.

(25)
The surgical support system according to (24), wherein, when the difference between the prognostic information and the standard data, corresponding to a type of surgery performed in the operating room, exceeds the second threshold value, the processing circuitry is further configured to control the output of the second warning information.

(26)
The surgical support system according to (23), wherein the processing circuitry is further configured to acquire information related to: cooperation between persons, information related to a position or a motion of each person, a duration of a surgery stage, or an elapsed time up to a predetermined stage in a surgery stage,
wherein the information, the duration, and the elapsed time are associated with each of a plurality of pieces of prognostic information when a difference between the plurality of pieces of prognostic information and the standard data exceeds the second threshold value and the plurality of pieces of prognostic information are extracted.

(27)
The surgical support system according to any one of (23) to (26), wherein the prognostic information includes at least one of: a hospitalization period of a patient, stability of a symptom of the patient after surgery, and information indicating a state of the patient after the surgery.

(28)
The surgical support system according to any one of (21) to (27), wherein the processing circuitry is further configured to compare the reference data that is related to a position of the reference person or the reference device in the operating room with first feature data indicating a position of the first person or the first device extracted from the first image.

(29)
The surgical support system according to (28), wherein the first feature data includes a plurality of positions through which the first person or the first device has passed or a center of gravity of the plurality of positions.

(30)
The surgical support system according to any one of (21) to (29), wherein when a surgery stage is recognized from the first image or from an image captured at a timing having a predetermined relation with a timing at which the first image is captured, the processing circuitry is further configured to compare the reference data corresponding to the surgery stage with the first feature data.

(31)
The surgical support system according to (30), wherein the surgery stage is recognized by detection of an event corresponding to the surgery stage.

(32)
The surgical support system according to any one of (21) to (31), wherein when second feature data related to a second person or a second device extracted from a second image is corrected, the reference data is updated based on the correction.

(33)
The surgical support system according to (32), wherein when a surgery stage is recognized from the second image or from an image captured at a timing having a predetermined relation with a timing at which the second image is captured, the reference data is updated to include reference data of the surgery stage.

(34)
The surgical support system according to (33), wherein the processing circuitry is further configured to control an output of third warning information when a transition order of the surgery stage differs between the reference data and the first feature data or when a difference in a duration of a corresponding surgery stage or an elapsed time, up to a corresponding stage, exceeds a third threshold value.

(35)
The surgical support system according to (31), wherein the reference data is updated to include information related to cooperation between persons when the cooperation between the persons is recognized from a third image.

(36)
The surgical support system according to (35), wherein the processing circuitry is configured to control an output of fourth warning information when at least one person of a group of a plurality of persons who cooperate with each other differs between the reference data and the first feature data as a result of one of the plurality of persons who cooperate with each other being switched, or as a result of a difference in a duration of cooperation between the plurality of persons, or an elapsed time of cooperation between the plurality of persons, up to a corresponding stage, exceeds a fourth threshold value.

(37)
The surgical support system according to any one of (21) to (36), wherein the processing circuitry is further configured to generate the reference data related to the reference person or the reference device in the operating room by observation of the operating room.

(38)
The surgical support system according to any one of (21) to (37), wherein the processing circuitry is further configured to extract the first feature data from the first image.

(39)
An information processing method, including:
  comparing, by a processor, reference data that is related to a reference person or a reference device in an operating room and that is generated from observation of the operating room, with feature data related to a first person or a first device extracted from the image captured by a camera installed in the operating room; and
  triggering an alarm warning of a potential issue in the operating room based on a result of the comparing.

(40)

An information processing apparatus, including:
processing circuitry configured to:
compare reference data that is related to a reference person or a reference device in an operating room and that is generated from observation of the operating room, with feature data related to a first person or a first device extracted from the image captured by a camera installed in the operating room, and
trigger an alarm warning of a potential issue in the operating room based on a result of the comparing.

(41)

A surgical support system, including:
a camera installed in an operating room; and
an information processing apparatus including processing circuitry configured to compare reference data that is related to at least one person or device in the operating room over time and that is generated from observation of the operating room, with first feature data related to a first person or a first device extracted from a first image captured by the camera installed in the operating room.

REFERENCE SIGNS LIST 10 information processing apparatus
112 feature data extracting unit
114 recognizing unit
116 learning unit
118 processing unit
120 analyzing unit
122 output control unit
20 operating room
31 surgeon
32 assistant
33 anesthesiologist
34 nurse
35 nurse
36 engineer
41 microscope
42 navigation system
43 MEP measuring device
44 instrument storage

The invention claimed is:

1. A surgical support system, comprising:
a camera in an operating room; and
an information processing apparatus including processing circuitry configured to:
extract first feature data related to a first person or a first device from a first image captured by the camera in the operating room;
acquire information related to cooperation between the first person and one or more second persons;
compare the first feature data to reference data related to at least one reference person or reference device, the reference data being generated from observation of the operating room and being updated to include information related to cooperation between the first person and the one or more second persons in the operating room and positions of the first person and the one or more second persons in the operating room; and
output first warning information on condition that the first feature data indicates that the first person cooperates with the one or more second persons differently from the reference data based on
a position of at least one of the first person and the one or more second persons is different from the reference data,
a difference in a duration of cooperation between the first person and the one or more second persons is different than a reference duration, or
an elapsed time of cooperation between the first person and the one or more second persons, up to a corresponding stage, exceeds a first threshold.

2. The surgical support system according to claim 1, wherein the processing circuitry is further configured to output second warning information when a difference between the reference data and the first feature data exceeds a second threshold value.

3. The surgical support system according to claim 1, wherein the processing circuitry is further configured to compare standard data with prognostic information associated with the first image.

4. The surgical support system according to claim 3, wherein the processing circuitry is further configured to output third warning information when a difference between the prognostic information and the standard data exceeds a third threshold value.

5. The surgical support system according to claim 4, wherein, when the difference between the prognostic information and the standard data, corresponding to a type of surgery performed in the operating room, exceeds the third threshold value, the processing circuitry is further configured to output the third warning information.

6. The surgical support system according to claim 4, wherein the processing circuitry is further configured to acquire information related to: information related to a position or a motion of each person, a duration of a surgery stage, or an elapsed time up to a predetermined stage in a surgery stage,
wherein the information, the duration, and the elapsed time are associated with each of a plurality of pieces of prognostic information when a difference between the plurality of pieces of prognostic information and the standard data exceeds the third threshold value and the plurality of pieces of prognostic information are extracted.

7. The surgical support system according to claim 3, wherein the prognostic information includes at least one of: a hospitalization period of a patient, stability of a symptom of the patient after surgery, and information indicating a state of the patient after the surgery.

8. The surgical support system according to claim 1, wherein the processing circuitry is further configured to
extract a position of the first person or the first device extracted from the first feature data; and
compare the reference data that is related to a position of the reference person or the reference device in the operating room with the position of the first person or the first device.

9. The surgical support system according to claim 8, wherein the first feature data includes a plurality of positions through which the first person or the first device has passed or a center of gravity of the plurality of positions.

10. The surgical support system according to claim 1, wherein the processing circuitry is further configured to
recognize a surgery stage from the first image or from an image captured at a timing having a predetermined relation with a timing at which the first image is captured, and
compare the reference data corresponding to the surgery stage with the first feature data.

11. The surgical support system according to claim 10, wherein the processing circuitry is configured to recognize the surgery stage by detecting an event corresponding to the surgery stage.

12. The surgical support system according to claim 1, wherein the processing circuitry is configured to update, on condition that when second feature data related to a second person or a second device from a second image is corrected, the reference data is updated based on the correction.

13. The surgical support system according to claim 12, wherein the processing circuitry is configured to update, on condition that when a surgery stage is recognized from the second image or from an image captured at a timing having a predetermined relation with a timing at which the second image is captured, the reference data is updated to include reference data of the surgery stage.

14. The surgical support system according to claim 13, wherein the processing circuitry is further configured to output fourth warning information when a transition order of the surgery stage differs between the reference data and the first feature data or when a difference in a duration of a corresponding surgery stage or an elapsed time, up to a corresponding stage, exceeds a fourth threshold value.

15. The surgical support system according to claim 1, wherein the processing circuitry is further configured to generate the reference data related to the reference person or the reference device in the operating room by observation of the operating room.

16. An information processing method, comprising:
    extracting feature data related to a first person or a first device extracted from an image captured by a camera in an operating room;
    acquiring information related to cooperation between the first person and one or more second persons;
    comparing the feature data to reference data related to at least one reference person or reference device, the reference data being generated from observation of the operating room and being updated to include information related to cooperation between the first person and the one or more second persons in the operating room and positions of the first person and the one or more second persons in the operating room; and
    triggering an alarm warning of a potential issue in the operating room on condition that the feature data indicates that the first person cooperates with the one or more second persons differently from the reference data based on
    a position of at least one of the first person and the one or more second persons is different from the reference data,
    a difference in a duration of cooperation between the first person and the one or more second persons is different than a reference duration, or
    an elapsed time of cooperation between the first person and the one or more second persons, up to a corresponding stage, exceeds a first threshold.

17. An information processing apparatus, comprising:
    processing circuitry configured to:
    extract first feature data related to a first person or a first device from a first image captured by a camera in an operating room;
    acquire information related to cooperation between the first person and one or more second persons;
    compare the first feature data to reference data related to at least one reference person or reference device, the reference data being generated from observation of the operating room and being updated to include information related to cooperation between the first person and the one or more second persons in the operating room and positions of the first person and the one or more second persons in the operating room; and
    trigger an alarm warning of a potential issue in the operating room on condition that the first feature data indicates that the first person cooperates with the one or more second persons differently from the reference data based on
    a position of at least one of the first person and the one or more second persons is different from the reference data,
    a difference in a duration of cooperation between the first person and the one or more second persons is different than a reference duration, or
    an elapsed time of cooperation between the first person and the one or more second persons, up to a corresponding stage, exceeds a first threshold.

18. A surgical support system; comprising:
    a camera in an operating room; and
    an information processing apparatus including processing circuitry configured to extract first feature data related to a first person or a first device from a first image captured by the camera in the operating room;
    extract first feature data related to a first person or a first device from a first image captured by the camera in the operating room;
    acquire information related to cooperation between the first person and one or more second persons;
    compare the first feature data to reference data related to at least one reference person or reference device, the reference data being generated from observation of the operating room and being updated to include information related to cooperation between the first person and the one or more second persons in the operating room and positions of the first person and the one or more second persons in the operating room; and
    output first warning information on condition that the first feature data indicates that the first person cooperates with the one or more second persons differently from the reference data based on
    a position of at least one of the first person and the one or more second persons is different from the reference data,
    a difference in a duration of cooperation between the first person and the one or more second persons is different than a reference duration, or
    an elapsed time of cooperation between the first person and the one or more second persons, up to a corresponding stage, exceeds a first threshold.

* * * * *